(12) United States Patent
Choo et al.

(10) Patent No.: US 9,196,471 B1
(45) Date of Patent: Nov. 24, 2015

(54) SCANNER FOR WAFERS, METHOD FOR USING THE SCANNER, AND COMPONENTS OF THE SCANNER

(75) Inventors: Yen Fui Choo, Hillsboro, OR (US); David Palsulich, Boise, ID (US)

(73) Assignee: Yen Fui Choo, Hillsboro, OR (US)

( * ) Notice: Subject to any disclaimer, the term of this patent is extended or adjusted under 35 U.S.C. 154(b) by 562 days.

(21) Appl. No.: 13/487,086

(22) Filed: Jun. 1, 2012

(51) Int. Cl.
*H01L 21/02* (2006.01)
*G01N 15/06* (2006.01)
*G01N 33/00* (2006.01)
*G01N 33/48* (2006.01)

(52) U.S. Cl.
CPC .................................. *H01L 21/02041* (2013.01)

(58) Field of Classification Search
CPC .. G01N 21/9501; G01N 21/956; G01N 21/94
USPC ..................... 422/68.1; 356/72, 237.3, 237.5; 257/E23.179
See application file for complete search history.

(56) References Cited

U.S. PATENT DOCUMENTS

| | | |
|---|---|---|
| 2,043,966 A | 6/1936 | Whiston et al. |
| 4,113,532 A | 9/1978 | Authier et al. |
| 4,316,430 A | 2/1982 | Jolly et al. |
| 4,466,872 A | 8/1984 | Einbinder |
| 4,510,177 A | 4/1985 | Furumura et al. |
| 4,535,227 A | 8/1985 | Shimizu |
| 4,709,655 A | 12/1987 | Van Mastrigt |
| 4,777,022 A | 10/1988 | Boldish et al. |
| 4,821,674 A | 4/1989 | deBoer et al. |
| 4,828,224 A | 5/1989 | Crabb et al. |
| 4,846,102 A | 7/1989 | Ozias |
| 5,063,031 A | 11/1991 | Sato |
| 5,283,437 A | 2/1994 | Greschner et al. |
| 5,474,612 A | 12/1995 | Sato et al. |
| 5,484,484 A | 1/1996 | Yamaga et al. |
| 5,595,606 A | 1/1997 | Fujikawa et al. |
| 6,045,617 A | 4/2000 | Keller |
| 6,074,202 A | 6/2000 | Yagi et al. |
| 6,132,519 A | 10/2000 | Ohashi et al. |
| 6,184,049 B1 | 2/2001 | Watanabe et al. |
| 6,443,826 B1 * | 9/2002 | Yang et al. .................... 451/388 |

(Continued)

FOREIGN PATENT DOCUMENTS

JP 2012-9475 A 1/2012

OTHER PUBLICATIONS

Definition of "Meniscus." The Great Soviet Encyclopedia, 3rd Edition, 1970-1979. <http://encyclopedia2.thefreedictionary.com/Meniscus>.*

(Continued)

*Primary Examiner* — Dennis M White
*Assistant Examiner* — Bryan Kilpatrick
(74) *Attorney, Agent, or Firm* — Law Office of Karen Dana Oster, LLC

(57) ABSTRACT

A horizontal scanner, a vertical scanner, and a dual-configuration scanner that is able to convert between a horizontal scanner and a vertical scanner is described herein.

27 Claims, 12 Drawing Sheets

(56) References Cited

U.S. PATENT DOCUMENTS

| | | | |
|---|---|---|---|
| 6,517,641 B2 * | 2/2003 | Fernandez | 134/33 |
| 7,002,144 B1 | 2/2006 | Palsulich et al. | |
| 7,241,701 B2 | 7/2007 | Dotsikas | |
| 7,732,225 B2 * | 6/2010 | Hanson et al. | 438/14 |
| 7,990,595 B1 | 8/2011 | Chou et al. | |
| 2002/0153482 A1 * | 10/2002 | Lin | 250/281 |
| 2004/0163670 A1 | 8/2004 | Ko et al. | |
| 2006/0035563 A1 * | 2/2006 | Kalenian et al. | 451/5 |
| 2009/0098290 A1 | 4/2009 | Watanabe et al. | |
| 2011/0139759 A1 | 6/2011 | Millman, Jr. et al. | |
| 2011/0147352 A1 | 6/2011 | Harte et al. | |

OTHER PUBLICATIONS

Benzinger, Jay Burton, "Organic Vapor Phase Deposition for Optoelectric Devices," Princeton University (www.princeton.edu/~benzinger/OVPD.pdf), at least as early as Apr. 3, 2012.

Sparks, Chris et. al., "A Novel Technique for Contamination Analysis of the Edge, the Bevel, and Edge Exclusion Area of 200 and 300mm Silicon Wafers," Sematech International, SPIE, Feb. 27, 2003.

Witvrouw, A. et. al., "A comparison between wet HF etching and vapor HF etching for sacrificial oxide removal," Proc. SPIE 4174, 130 (2000).

* cited by examiner

SCANNER FOR WAFERS, METHOD FOR USING THE SCANNER, AND COMPONENTS OF THE SCANNER

BACKGROUND OF THE INVENTION

Described herein are scanners for scanning wafers, methods for scanning wafers using the scanners, and components of the scanners, wherein the scanner may be, for example, a hydrophilic bulk bevel scanner.

Semiconductor fabrication is a multi-step manufacturing process including, for example, cleaning (e.g. using weak acids to remove unwanted particles), deposition (e.g. physical vapor deposition (PVD), chemical vapor deposition (CVD), and electromechanical deposition (ECD)), removal processes (e.g. wet etching, dry etching, and chemical-mechanical planarization (CMP)), patterning (e.g. lithography), and modification of electrical properties (e.g. doping and ion implantation). In an exemplary phase deposition processes, a vaporized chemical (e.g. $SiH_4$, $SiH_2Cl_2$, $SiHCl_4$, $SiCl_4$, $Si_2H_6$, etc.) may be condensed onto a wafer (also referred to as a substrate or a slice). The finished semiconductors are then separated (e.g. using dicing) into individual microcircuits for use in the fabrication of microelectronic devices, including but not limited to integrated circuits, solar devices, LEDs, flash, DRAM, memories.

Even in very small proportions, the presence of contaminants (e.g. heavy metals, oxides, nitrides, etc.) on wafers may decrease and/or destroy the function of downstream microelectronic devices. Generally at least one wafer per batch of wafers is tested for the presence and/or quantity of contaminants as part of the manufacturing process.

In order to test for contaminants on a wafer, a liquid may be brought into contact with the surface of the wafer. If contaminants are present on the wafer surface, at least some of the contaminants will be diffused or otherwise transferred into the liquid. After the liquid contacts the wafer surface, it may then be analyzed for the presence of contaminants. If contaminants are found on a wafer, the batch may be pulled from distribution or cleaned to prevent issues in functionality of downstream microelectronic devices.

One method and device for testing for contaminants on a wafer is described in Japanese Patent No. JP2012-9475A. This reference describes the use of a droplet of liquid, such as a droplet of hydrogen fluoride (HF), being placed on an upper surface of a wafer held in horizontal orientation. During contaminant testing, the droplet is moved across the upper surface of the wafer. The droplet is then collected and analyzed for the presence of contaminants. This method and device may be problematic in that the droplet may spread out and/or adhere to the surface of the wafer if the wafer is hydrophilic, making collection and analysis of the drop difficult. Further, the wafer may only be analyzed in a horizontal position and therefore only a bulk (i.e. planar surface) portion of the wafer is tested for contamination. Further still, the movement pattern of the droplet may be unpredictable and sample from only a small portion of the wafer surface.

In another method and device for testing for wafer contamination from the non-patent literature publication "A Novel Technique for Contamination Analysis of the Edge, the Bevel, and the Exclusion Area of 200 and 300 mm Silicon Wafers" by Chris Sparks et al. from International SEMATECH (hereinafter referred to as "Sparks"), a wafer is held in a vertical orientation. A sample boat containing liquid may be raised to the edge of the wafer so that the wafer is at least partially submerged into the liquid within the sample boat, below an upper edge of the sample boat. The liquid is then collected in a 0.5 mL sample vial and analyzed by a scanning device (Technos 630T nine point TXRF analysis). This method and device may be problematic in that it requires a relatively large liquid sample, which may be a hazardous material. Further, the wafer may only be analyzed in a vertical orientation and, therefore, only the beveled edge and/or surfaces close to the beveled edge of the wafer will be tested for contamination.

BRIEF SUMMARY OF THE INVENTION

Described herein are scanners for scanning wafers, methods for scanning wafers using the scanners, and components of the scanners, wherein the scanner may be, for example, a hydrophilic bulk bevel scanner.

A first preferred exemplary scanner is for scanning at least one wafer having an upper surface, a lower surface, and a peripheral edge. Preferably the scanner includes a droplet cup with a droplet cup tip, the droplet cup tip having a concave tip well with an uppermost surface, the tip well suitable for holding a droplet of testing reagent so that at least part of the droplet is above the uppermost surface of the droplet cup tip. Preferably the scanner also includes wafer positioning and rotating structure suitable for positioning the wafer above the droplet cup tip such that at least part of the wafer contacts the at least part of the droplet above the uppermost surface of the droplet cup tip. During a scanning process there is relative movement between the droplet and the wafer.

Surface tension may cause the at least part of the droplet to be held above the uppermost surface of the droplet cup tip.

The scanner may be a dual-configuration scanner that converts between a horizontal scanner for scanning the lower surface of the wafer and a vertical scanner for scanning the peripheral edge of the wafer. Alternatively, the scanner may be a horizontal scanner for scanning the lower surface of the wafer in a horizontal orientation. Another alternative is that the scanner may be a vertical scanner for scanning the peripheral edge of the wafer in a vertical orientation.

If the scanner is a horizontal scanner or a dual-configuration scanner, when the wafer is in a horizontal orientation, the relative movement between the droplet and the wafer creates a pattern therebetween.

Preferred exemplary scanners may include liquid transfer structures for transferring the droplet of testing reagent from at least one reagent container to the tip well, at least one alignment peg for aligning the wafer in a horizontal orientation, and/or at least one self-cleaning or self-sterilizing alignment peg.

A second preferred exemplary scanner is designed to scan at least one wafer having an upper surface, a lower surface, and a peripheral edge. This exemplary scanner includes a droplet of testing reagent and wafer positioning and rotating structure for positioning a wafer in a horizontal orientation above the droplet such that at least part of the lower surface of the wafer contacts at least part of the droplet. During the scanning process there is relative movement between the droplet and the wafer. The droplet of testing reagent may be positioned within a tip well of a droplet cup tip of a droplet cup, the tip well having an uppermost surface, the droplet of testing reagent positioned within the tip well such that at least part of the droplet is above the uppermost surface of the droplet cup tip, at least part of a lower surface of the wafer contacting the at least part of the droplet above the uppermost surface.

The scanner may be a dual-configuration scanner in which the wafer positioning and rotating structure transitions between positioning the wafer in the horizontal orientation and positioning the wafer in a vertical orientation for scanning the peripheral edge of the wafer.

The relative movement between the droplet and the wafer may create a pattern therebetween.

The scanner may also include at least one liquid transfer structure for transferring the droplet of testing reagent from at least one reagent container to the tip well and/or at least one self-cleaning or self-sterilizing alignment peg for aligning the wafer.

A second preferred exemplary scanner is a dual-configuration scanner for scanning at least one wafer having an upper surface, a lower surface, and a peripheral edge. The dual-configuration scanner includes testing reagent and wafer positioning and rotating structure for positioning a wafer above the testing reagent such that at least part of the wafer contacts at least part of the testing reagent. The wafer positioning and rotating structure can transition the wafer between a horizontal orientation and a vertical orientation. The wafer positioning and rotating structure can rotate the wafer in the horizontal orientation such that there is relative movement between the testing reagent and the lower surface the wafer during a scanning process. The wafer positioning and rotating structure rotates the wafer in the vertical orientation such that there is relative movement between the testing reagent and the peripheral edge the wafer during a scanning process.

In the dual-configuration scanner, the testing reagent may be a droplet of testing reagent. The testing reagent may also be a droplet of testing reagent within a tip well of a droplet cup tip of a droplet cup, the tip well having an uppermost surface, the droplet of testing reagent positioned within the tip well such that at least part of the droplet is above the uppermost surface of the droplet cup tip.

The subject matter described herein is particularly pointed out and distinctly claimed in the concluding portion of this specification. Objectives, features, combinations, and advantages described and implied herein will be more readily understood upon consideration of the following detailed description of the invention, taken in conjunction with the accompanying drawings.

BRIEF DESCRIPTION OF THE SEVERAL
VIEWS OF THE DRAWINGS

The accompanying drawings illustrate various exemplary scanners and/or provide teachings by which the various exemplary scanners are more readily understood.

Figure 1:
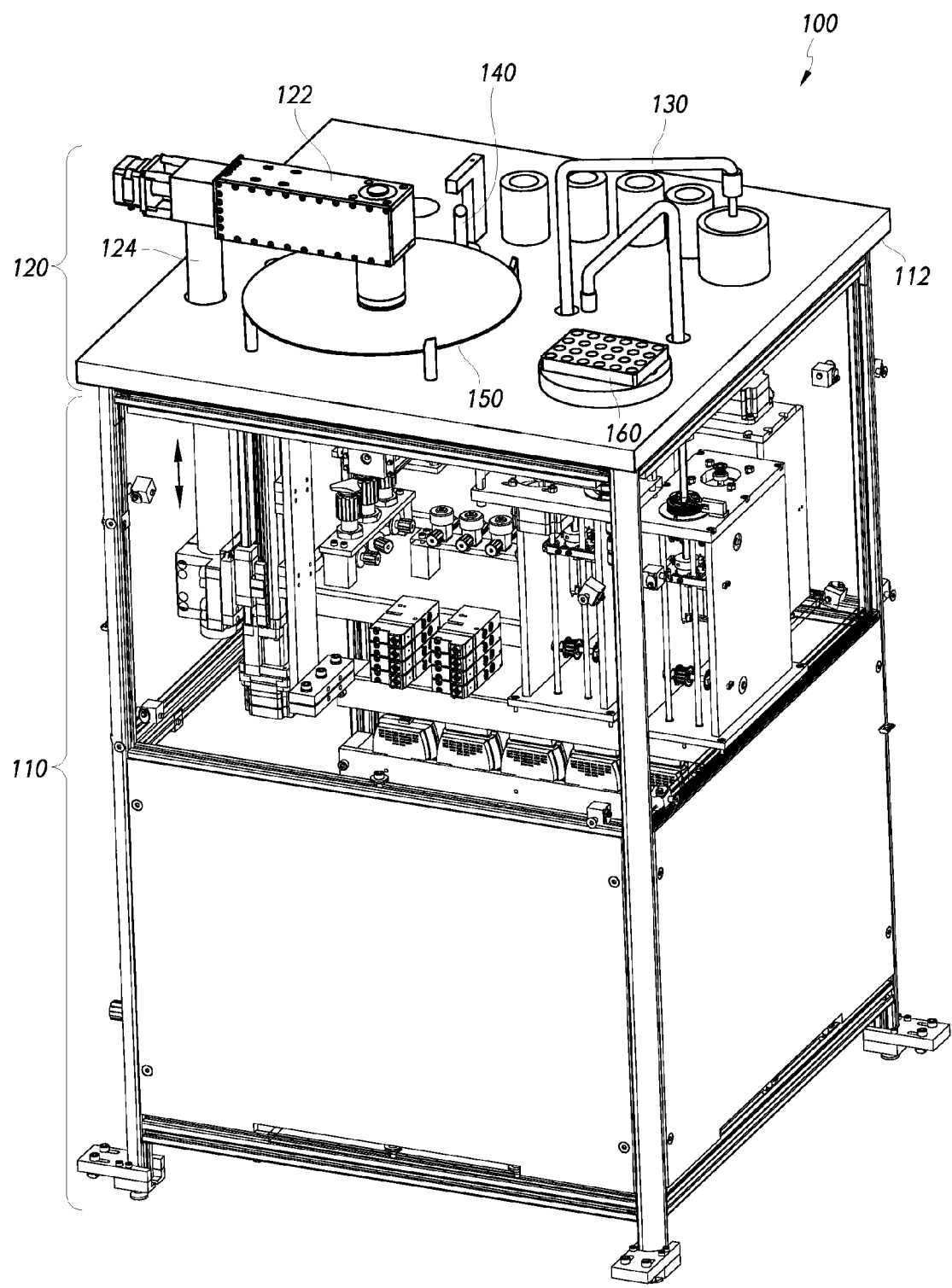
FIG. 1 is a perspective view of an exemplary horizontal scanner or a dual-configuration scanner in a horizontal configuration, having a wafer held in a horizontal orientation.

The drawing figures are not necessarily to scale. Certain features or components herein may be shown in somewhat schematic form and some details of conventional elements may not be shown or described in the interest of clarity and conciseness. The drawing figures are hereby incorporated in and constitute a part of this specification.

DETAILED DESCRIPTION OF THE INVENTION

Described herein are a horizontal scanner (FIGS. 1-5), a vertical scanner (FIGS. 6-9), and a dual-configuration scanner (FIGS. 1-9) that is able to convert between a horizontal scanner and a vertical scanner. Each of the scanners takes advantage of a droplet cup with a concave tip well in its droplet cup tip (the top portion of the droplet cup, variations of which are shown in FIGS. 10A-10I). The tip well holds a droplet of testing reagent so that at least part of the droplet is above the uppermost surface of the droplet cup tip of the droplet cup. One advantage to the shown tip well design in which scanning is performed on the bottom surface of the wafer is that the droplet of testing reagent stays with the tip well so that cross contamination is less of an issue than with scanners that scan from the top surface of the wafer.

The exemplary scanners disclosed herein may be better understood with reference to the drawings, but these scanners are not intended to be of a limiting nature. The same reference numbers will be used throughout the drawings and description in this document to refer to the same or like parts.

DEFINITIONS

Before describing the scanners and the figures, some of the terminology should be clarified. Please note that the terms and phrases may have additional definitions and/or examples throughout the specification. Where otherwise not specifically defined, words, phrases, and acronyms are given their ordinary meaning in the art. The following paragraphs provide some of the definitions for terms and phrases used herein.

The term "wafer" refers to known (also referred to as a substrate or a slice) semiconductor material used in the fabrication of integrated circuits and other microdevices. Unless specifically specified otherwise, "wafer" refers to all wafers of all sizes and materials known or yet to be discovered.

The term "hydrophilic" is defined to mean "having a strong affinity for water" or "water attracting." The surface of a wafer is hydrophilic. Scanning using a hydrophilic scanner takes advantage of the attraction between the droplet of testing reagent 142, 242 (which has properties similar to water) and the surface of the wafer 150, 250. However, because the droplet surface area that contacts the tip well 144, 244 is greater than the droplet surface area that contacts the wafer 150, 250, the droplet 142, 242 remains in the tip well 144, 244 during contamination scanning. Although the scanner shown and described herein is a hydrophilic scanner, an alternative scanner could be a hydrophobic scanner.

The phrase "surface tension" is used to describe the property of the surface of a liquid that allows it to resist an external force. The molecules of the droplet of testing reagent 142, 242 have a strong attraction to each other that prevent the droplet of testing reagent 142, 242 from spreading out. Instead, the upper surface of the droplet 142, 242 keeps a substantially convex shape. This allows the droplet of testing reagent 142, 242 to sit in a concave tip well 144, 244 so that at least part of the droplet 142, 242 is above the uppermost surface of the tip of the droplet cup 140, 240. (This can be seen in FIG. 9.)

The term "scanning" is used to define the testing process for contamination performed by the scanner on a wafer (also referred to as a substrate or a slice). The scanning may be accomplished using the shown hydrophilic scanner or, alternatively, a hydrophobic scanner.

Figure 5A:
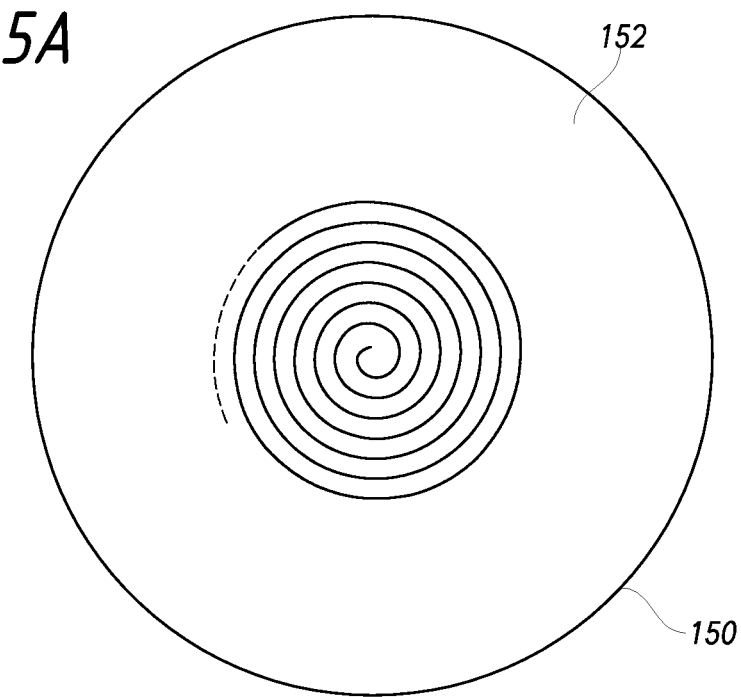
FIG. 5A is a plan view of the lower surface of a wafer showing a spiral scanning pattern originating from the center of the wafer created by the relative movement between the droplet and the wafer.
Figure 5B:
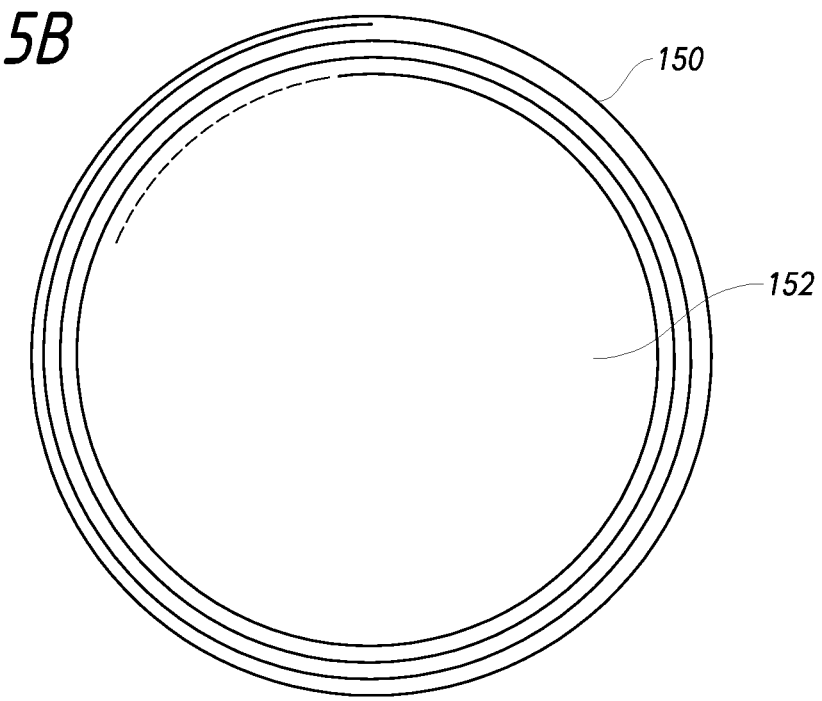
FIG. 5B is a plan view of the lower surface of a wafer showing a spiral scanning pattern originating from the peripheral edge of the wafer created by the relative movement between the droplet and the wafer.

The phrase "relative movement" is meant to describe the fact that one or both of the droplet of testing reagent 142, 242 and/or a surface of the wafer 150, 250 are moving relative to the other. In other words, the droplet 142, 242 may move (e.g. due to the rotation or lateral movement of the droplet cup 140, 240) and/or the surface of the wafer 150 may move (e.g. due to the rotation of the axel 121, 221 and/or wafer 150, 250). By changing the relative movement, the pattern on the wafer 150, 250 may be changed. FIGS. 5A and 5B show exemplary patterns created by relative movement between the droplet of testing reagent 142, 242 and/or a surface of the wafer 150, 250. A pattern encompassing the entire peripheral edge 154, 254 would be created by relative movement described in association with the vertical scanner 200 or the vertical configuration of a dual-configuration scanner 100, 200.

The scanner described herein may have associated hardware, software, and/or firmware (a variation, subset, or hybrid of hardware and/or software). The term "hardware" includes at least one "processing unit," "processor," "computer," "programmable apparatus," and/or other device capable of executing instructions or steps known or yet to be discovered. The term "software" includes at least one "program," "subprogram," "series of instructions," or hardware instructions or hardware-readable program code known or yet to be discovered. Software may be loaded onto hardware (or firmware) to produce a machine, such that the software executes on the hardware to create structures for implementing the functions described herein. Further, the software may be loaded onto the hardware (or firmware) so as to direct the scanner to function in a particular manner described herein or to perform a series of operational steps as described herein. The phrase "loaded onto the hardware" also includes being loaded into memory associated with or accessible by the hardware. The term "memory" is defined to include any type of hardware (or other technology)-readable media (also referred to as machine-readable storage medium) including, but not limited to attached storage media (e.g. hard disk drives, network disk drives, servers), internal storage media (e.g. RAM, ROM, EPROM, FLASH-EPROM, or any other memory chip or cartridge), removable storage media (e.g. CDs, DVDs, flash drives, memory cards, floppy disks, flexible disks), firmware, and/or other storage media known or yet to be discovered. Depending on its purpose, the memory may be transitory and/or non-transitory. Appropriate "communications," "signals," and/or "transmissions" (which include various types of information and/or instructions including, but not limited to data, commands, bits, symbols, voltages, currents, electromagnetic waves, magnetic fields or particles, optical fields or particles, and/or any combination thereof) over appropriate "communication paths," "transmission paths," and other means for signal transmission (including any type of connection between two elements on the system (the system including, for example, scanners, hardware systems and subsystems, and memory) would be used as appropriate to facilitate controls and communications.

The term "associated" is defined to mean integral or original, retrofitted, attached, connected (including functionally connected), positioned near, and/or accessible by.

It should be noted that some terms used in this specification are meant to be relative. For example, the terms "horizontal plane" (x-y plane) and "vertical plane" (y-z plane) are meant to be relative.

Unless specifically stated otherwise, the terms "first," "second," and "third" are meant solely for purposes of designation and not for order or limitation.

It should be noted that the terms "may," "might," "can," and "could" are used to indicate alternatives and optional features and only should be construed as a limitation if specifically included in the claims. It should be noted that the various components, features, steps, or embodiments thereof are all "preferred" whether or not it is specifically indicated. Claims not including a specific limitation should not be construed to include that limitation.

Unless specifically stated otherwise, the term "exemplary" is meant to indicate an example, representative, and/or illustration of a type. The term "exemplary" does not necessarily mean the best or most desired of the type.

It should be noted that the terms term "top" and "upper" are meant to be relative to the terms "bottom" and "lower." For example, the lower surface 152, 252 of a wafer 150, 250 is relative to the upper surface 153, 253 of a wafer 150, 250. Similarly, the term "front" is meant to be relative to the term "back."

It should be noted that, unless otherwise specified, the term "or" is used in its nonexclusive form (e.g. "A or B" includes A, B, A and B, or any combination thereof, but it would not have to include all of these possibilities). It should be noted that, unless otherwise specified, "and/or" is used similarly (e.g. "A and/or B" includes A, B, A and B, or any combination thereof, but it would not have to include all of these possibilities). It should be noted that, unless otherwise specified, the terms "includes" and "has" mean "comprises" (e.g. a device that includes, has, or comprises A and B contains A and B, but optionally may contain C or additional components other than A and B). It should be noted that, unless otherwise specified, the singular forms "a," "an," and "the" refer to one or more than one, unless the context clearly dictates otherwise.

Figure 6:
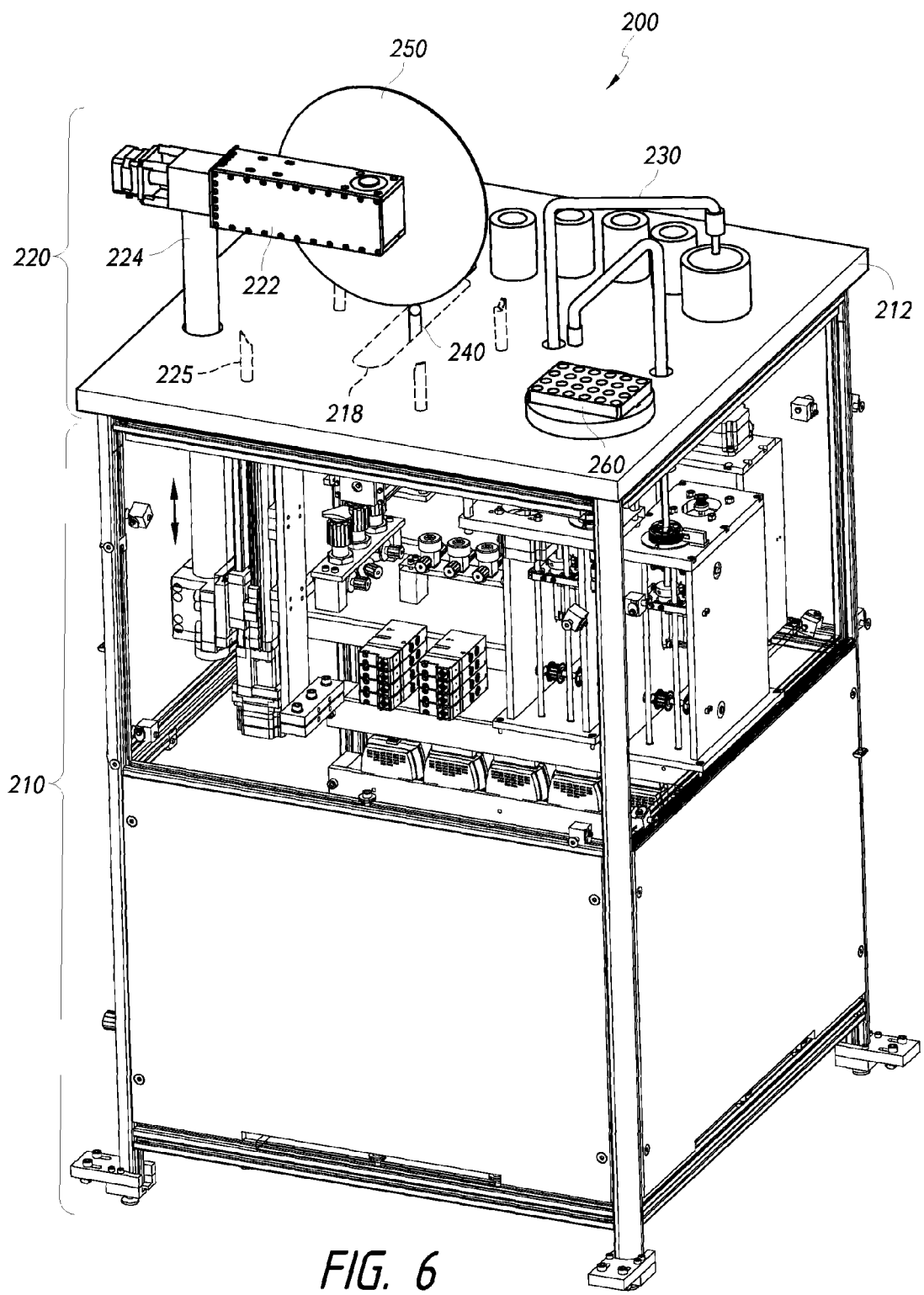
FIG. 6 is a perspective view of an exemplary vertical scanner or a dual-configuration scanner in a vertical configuration, having a wafer held in a vertical orientation.
Figure 11:
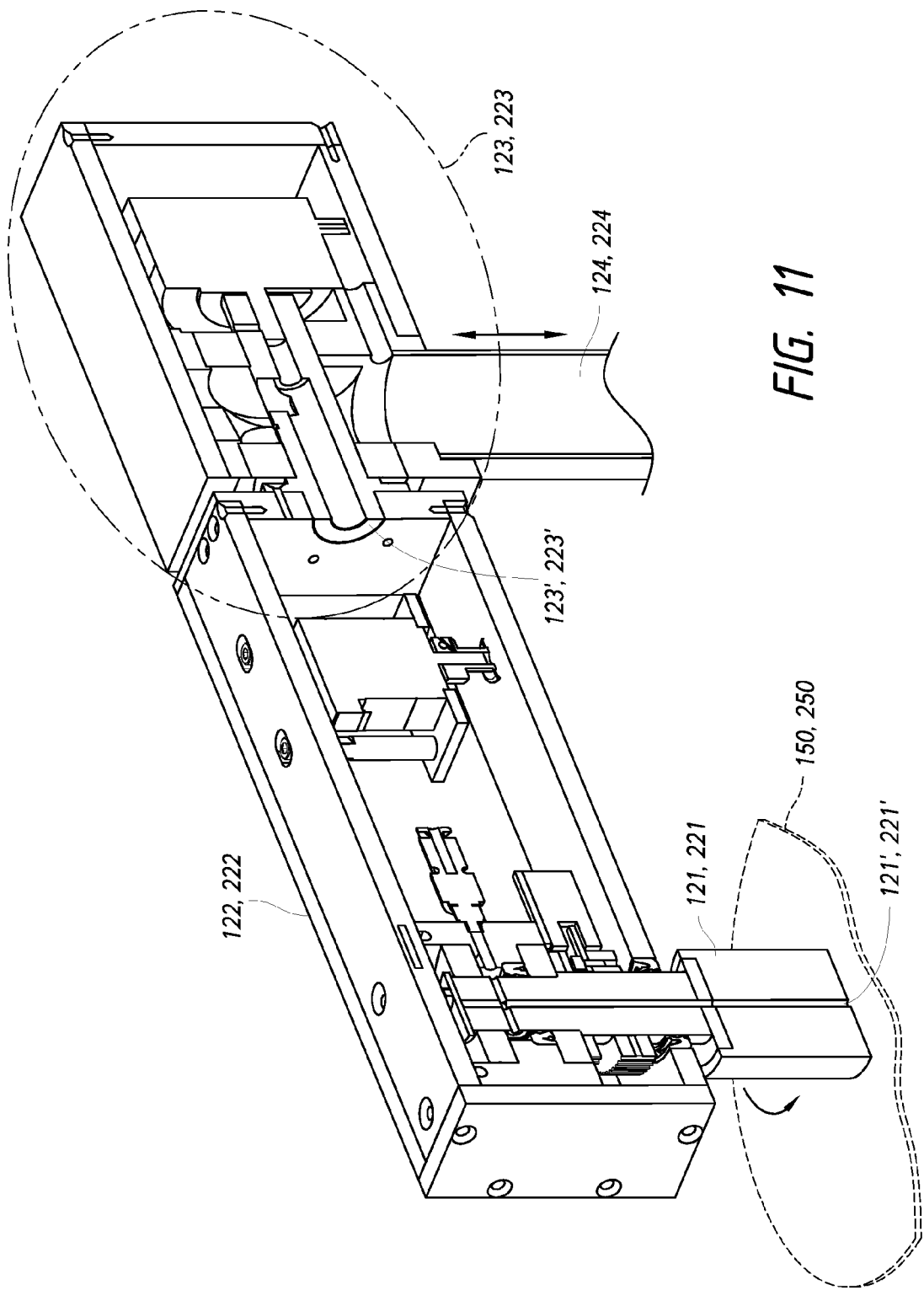
FIG. 11 is a cross-sectional view of exemplary internal structure of some of the wafer positioning and rotating structures such as the wafer axel, the wafer support arm, the support/lift interconnection, and the wafer lift shaft.

Overview of the Scanner(s):

FIGS. 1 and 6 show either two distinct scanners 100 and 200 or a single scanner 100, 200 having two configurations. The scanner 100 of FIG. 1 scans a wafer 150 in a horizontal orientation. The scanner 200 of FIG. 6 scans a wafer 250 in a vertical orientation. FIGS. 1 and 6 may also show two configurations of a single scanner that is able to convert between scanning a wafer in the horizontal orientation and scanning a wafer in the vertical orientation. FIG. 11 shows exemplary internal workings of the exemplary internal structures of components used to implement an exemplary dual-configuration that has two configurations. A dual-configuration scanner has the advantage of being able to use a single scanner device to scan both the edge of the wafer 150 and the lower surface of the wafer 150. These advantages include, but are not limited to economic and versatility advantages to both producing a single dual-configuration scanner device (e.g. the economics of mass production) and using a single dual-configuration scanner device (e.g. companies can repurpose as needed). The conversion between orientations may be accomplished manually or the conversion between orientations may be automated. It should be noted that descriptions of two separate scanners should also be considered as two configurations of the same dual-configuration scanner.

Figure 2:
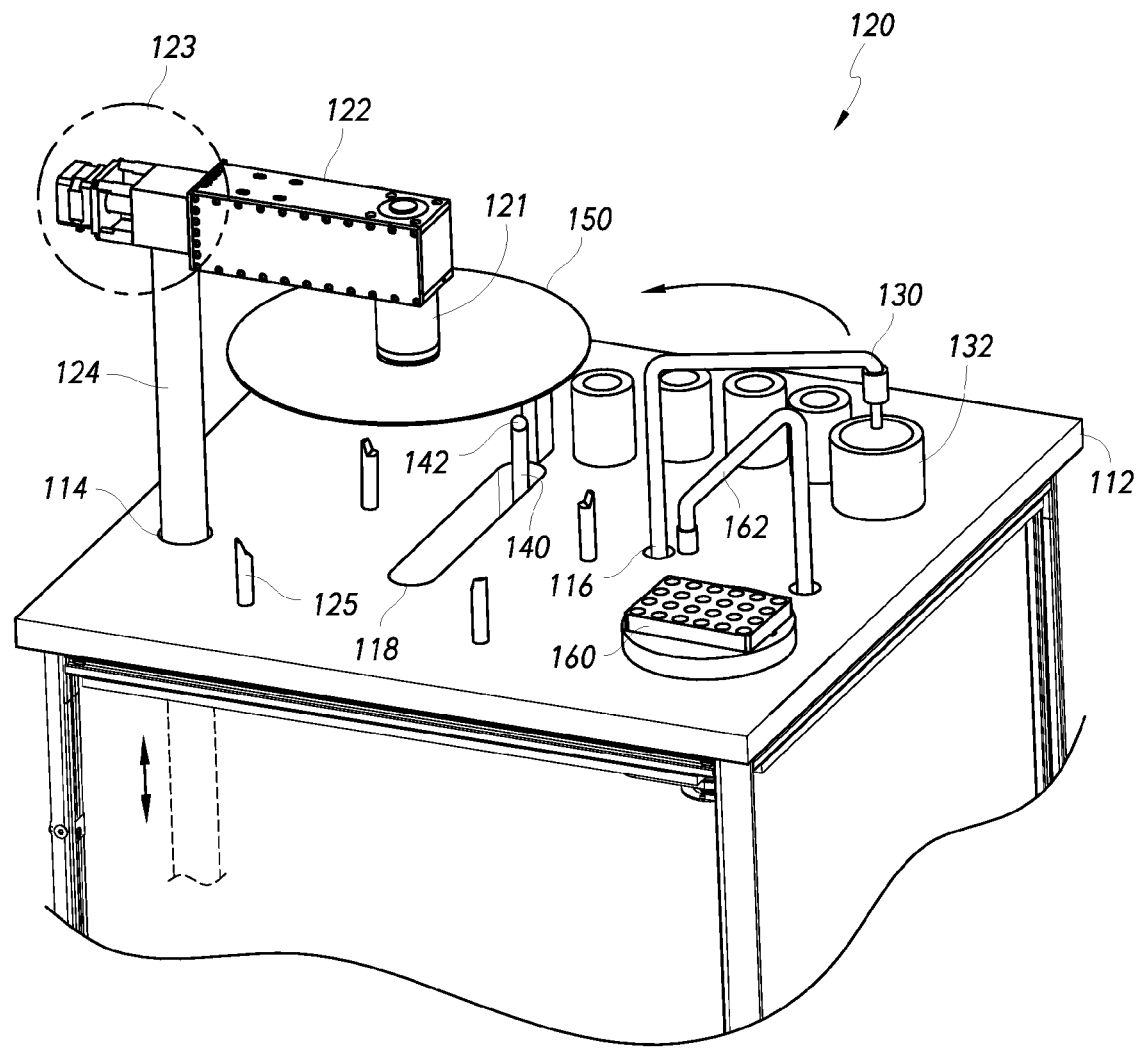
FIG. 2 is a perspective view of the applied workings of the exemplary horizontal scanner of FIG. 1, showing the wafer and the droplet cup in a wafer-loading position.
Figure 3:
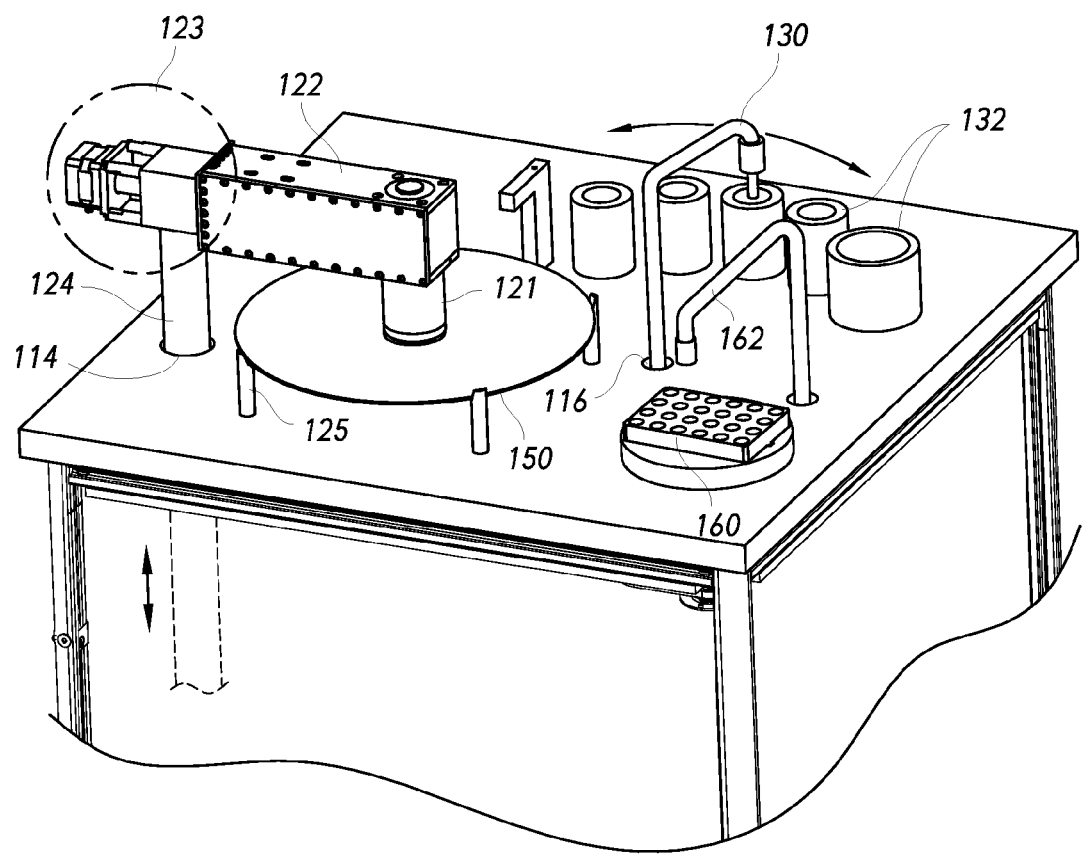
FIG. 3 is a perspective view of the applied workings of the exemplary horizontal scanner of FIG. 1 showing the wafer and the droplet cup in a contaminant-testing position.
Figure 7:
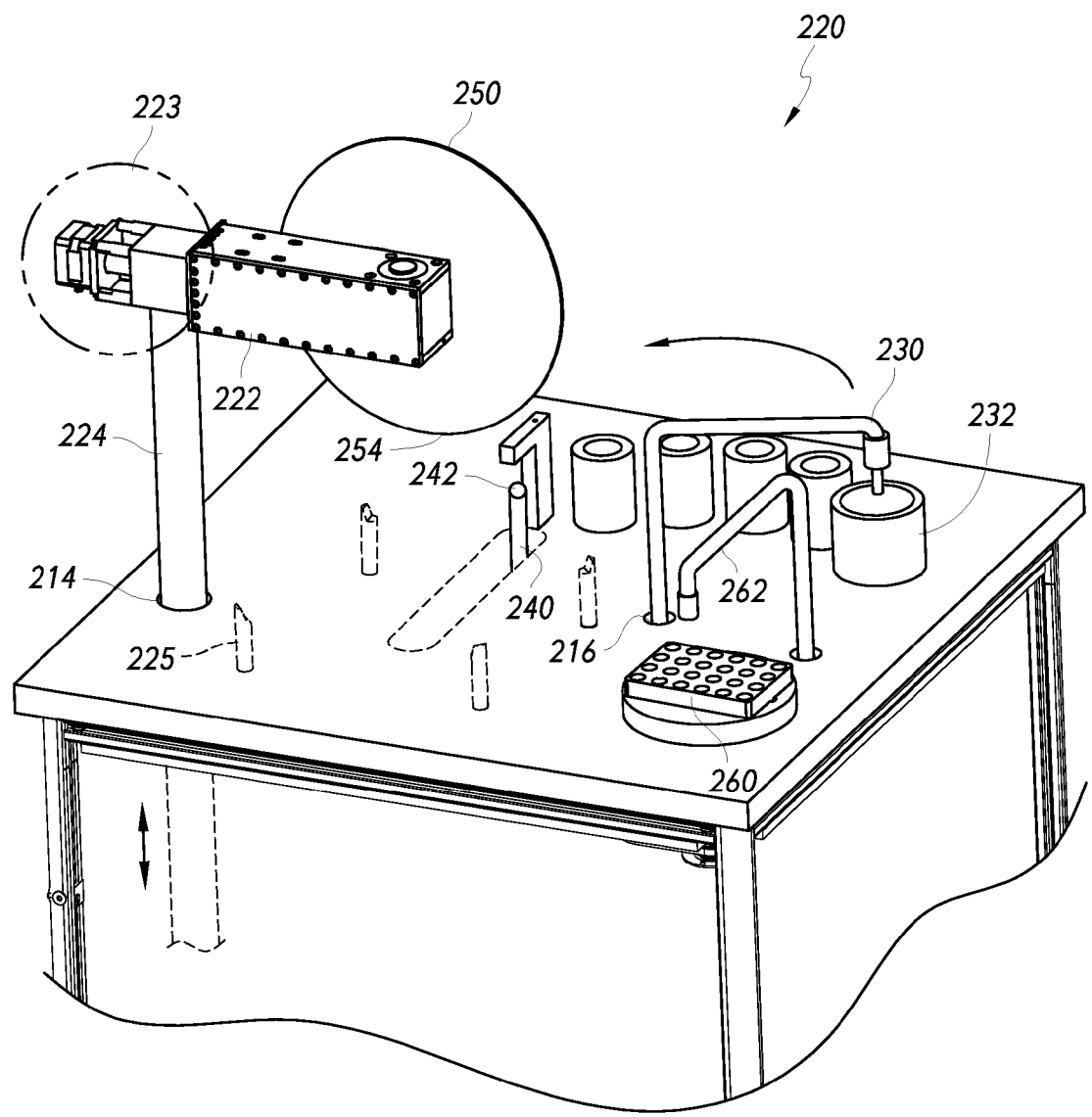
FIG. 7 is a perspective view of the applied workings of the exemplary vertical scanner of FIG. 6 showing the wafer and the droplet cup in a wafer-loading position.
Figure 8:
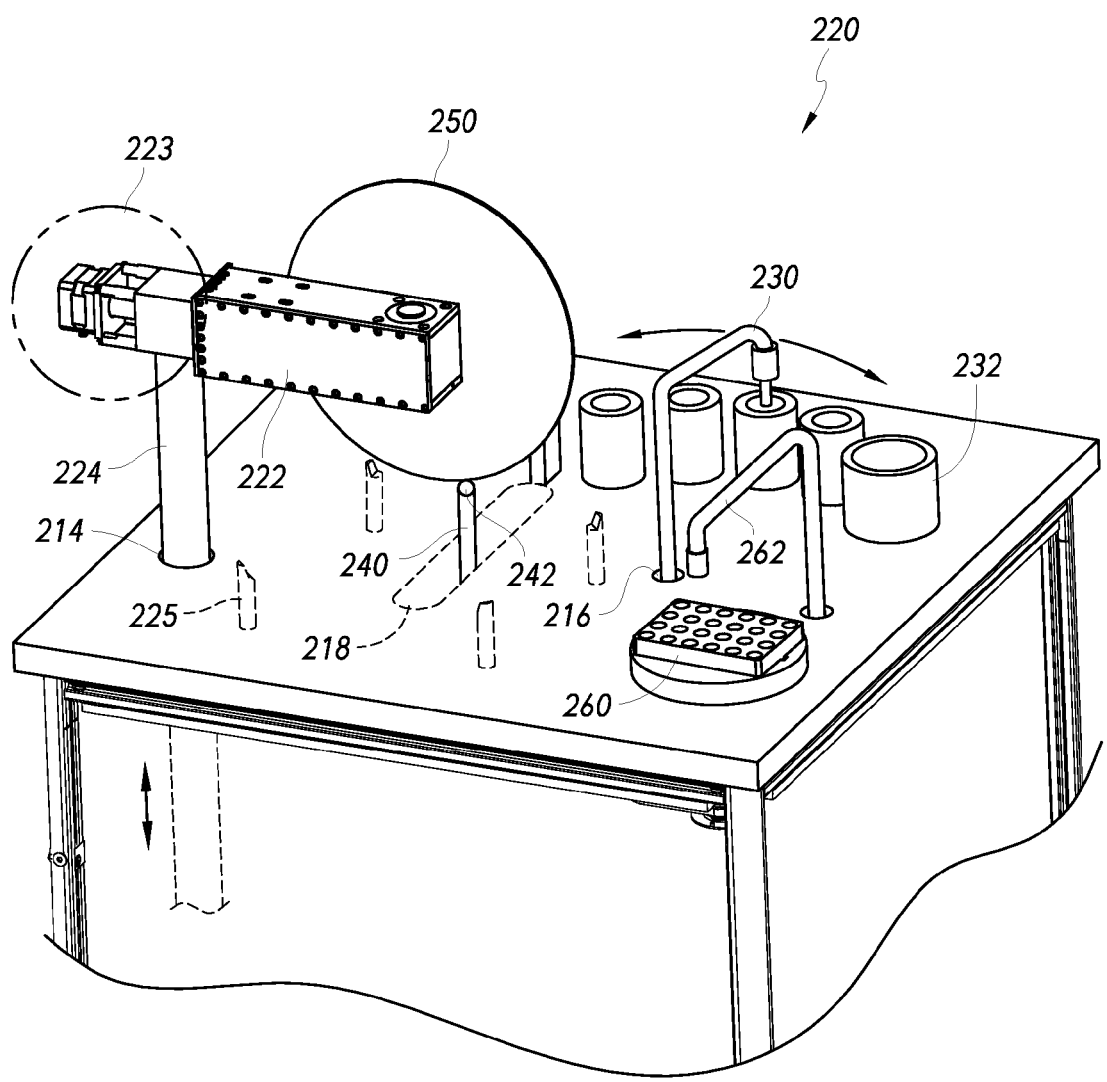
FIG. 8 is a perspective view of the applied workings of the exemplary vertical scanner of FIG. 6 showing the wafer and the droplet cup in a contaminant-testing position.

For purposes of description, scanners 100, 200 can be divided into internal workings 110, 210 and applied workings 120, 220. The internal workings 110 are the behind-the-scenes mechanical and electrical components that cause the applied workings 120, 220 to function as described herein. The internal workings 110, 210 of the scanners 100, 200 are shown for exemplary purposes only and may have alternate configurations, may include different components, and/or may perform their respective functions in alternative ways. FIG. 2 shows detailed exemplary applied workings 120 of the scanner 100 in the wafer-loading position, FIG. 3 shows detailed exemplary applied workings 120 of the scanner 100 in the contaminant-testing position, FIG. 7 shows detailed exemplary applied workings 220 of the scanner 200 in the wafer-loading position, FIG. 8 shows detailed exemplary applied workings 220 of the scanner 200 in the contaminant-testing position. FIGS. 1 and 6 show exemplary scanners 100, 200 with applied workings 120, 220 (the sampling and testing portion) towards or at the top of the scanners 100, 200 and the internal workings 110, 210 below the applied workings 120, 220 and internal to the scanners 100, 200. A flat surface or table 112, 212 may divide the internal workings 110, 210 from the applied workings 120, 220. The physical relationship between the internal workings 110, 210 and the applied workings 120, 220 is shown for exemplary purposes only and alternative scanners may have alternate configurations including, but not limited to having the internal workings above the applied workings, the applied workings both above and below the internal workings, or a vertical division in which the internal workings are behind or in front of the applied workings. Although not specifically shown, appropriate software, hardware, and/or firmware may be used for controlling the scanners (including the internal workings 110, 210 and/or the applied workings 120, 220).

The applied workings 120, 220 include, for example, wafer positioning and rotating structures (e.g. a wafer axel 121 (not shown in the vertical arrangement, although it would be present and is referred to as wafer axel 221), a wafer support arm 122, 222, a support/lift interconnection 123, 223, a wafer lift shaft 124, 224, and alignment pegs 125, 225), liquid transfer structures (e.g. liquid transfer pipette arm 130, 230 and at least one reagent container 132, 232), testing structures (e.g. a droplet cup 140, 240 and a droplet of testing reagent 142, 242), and analysis structures (e.g. at least one sample tray 160, 260). The wafer positioning and rotating structures together are used to correctly position the wafer 150, 250 in relation to the testing structure and then to rotate the wafer 150, 250 either horizontally or vertically. The liquid transfer structures together transfer the liquid necessary for the scanning procedure to the testing structure and then, after scanning, remove the liquid from the testing structure and transfer it to the analysis structure.

Preferred wafer positioning and rotating structures may include a wafer axel 121, 221, a wafer support arm 122, 222, a support/lift interconnection 123, 223, a wafer lift shaft 124, 224, and alignment pegs 125, 225. Although shown generally throughout the drawings, FIG. 11 shows detailed exemplary internal structure of some of the wafer positioning and rotating structures such as the wafer axel 121, 221, the wafer support arm 122, 222, the support/lift interconnection 123, 223, and the wafer lift shaft 124, 224. As set forth above, the wafer positioning and rotating structures together are used to correctly position the wafer 150, 250 in relation to the testing structure and then to rotate the wafer 150, 250 either horizontally or vertically. A wafer axel 121, 221 is centrally (and preferably removably) attached or affixed to the wafer 150, 250. The actual attachment may be accomplished using, for example, adhesives, vacuum, mechanical attachment mechanisms, or any other attachment means known or yet to be discovered. (The exemplary structure shown in FIG. 11 includes a passage 121', 221' through the wafer axel 121, 221 through which vacuum can be asserted on the surface of the wafer 150, 250.) As shown, when the wafer axel rotates in relation to the wafer support arm 122, 222, the wafer 150, 250 rotates. For a dual-configuration scanner, the wafer support arm 122, 222 and wafer axel 121, 221 may be transitioned between (converted) the horizontal and vertical orientations using the support/lift interconnection 123, 223 that attaches the wafer support arm 122, 222 to the wafer lift shaft 124, 224. (The exemplary structure shown in FIG. 11 includes a shaft 123', 223' that rotates at least a quarter of a turn (90°) to cause the wafer support arm 122, 222 to rotate at least a quarter of a turn (90°) so that the wafer 150, 250 can be positioned horizontally or vertically. The transition (conversion) between horizontal and vertical may be automated such that a motor rotates the shaft 123', 223' which, in turn, rotates the wafer support arm 122, 222 and the attached wafer axel 121, 221. Appropriate software, hardware, and/or firmware may be used to control electrical and/or mechanical components including, but not limited to rotation of the wafer support arm 122, 222, motor direction and speed, the vacuum applied to the wafer 150, 250, and/or rotation of the wafer axel 121, 221.) The wafer lift shaft 124, 224 may be used to raise and/or lower the wafer support arm 122, 222 and other structures to allow for attachment and removal of the wafer 150, 250 to the wafer axel 121, 221. The wafer lift shaft 124, 224 may extend through an aperture 114, 214 in the table 112, 212 be raised and/or lowered by internal workings 110, 210 such as suitable mechanical structure, hydraulic structure, pneumatic structure, manual structure, and/or other raising or lowering means known or yet to be discovered. The optional alignment pegs 125, 225 may be used to further assist in the positioning of the wafer 150 when it is in the horizontal orientation. (Alignment pegs 125, 225 are discussed in more detail in a dedicated subsection herein.) It should be noted that the wafer positioning and rotating structures is meant to be exemplary and alternatives might eliminate or alter the specific structures shown and described.

The testing structures include, for example, a droplet cup 140, 240 (having a tip well 144, 244) and a droplet of testing reagent 142, 242 (positioned within the tip well 144, 244). As will be discussed, the liquid transfer pipette arm 130, 230 deposits the droplet 142, 242 in the tip well 144, 244 of the droplet cup 140, 240. The droplet cup 140, 240 may be, for example, raised and/or lowered, rotated, movably positioned within the slot 118, 218, or otherwise adjusted (all of which will be generally referred to as "adjusting" or "adjustments"). The adjusting of the droplet cup 140, 240 may be performed by the internal workings 110, 210 such as one or more of a suitable a mechanical structure, a hydraulic structure, a pneumatic structure, a manual structure, and/or other adjustment movement means known or yet to be discovered.

Preferred liquid transfer structures may include at least one liquid transfer pipette arm 130, 230 and at least one reagent container 132, 232. The liquid transfer pipette arm 130, 230 may extend through an aperture 116, 216 in the table 112, 212, and be raised, lowered, and/or pivoted by the internal workings 110, 210 such as one or more of a suitable mechanical structure, a hydraulic structure, a pneumatic structure, a manual structure, and/or other raising or lowering means known or yet to be discovered. The liquid transfer pipette arm 130, 230 transfers the liquid necessary for the scanning procedure from the reagent container(s) 132, 232 in the form of a droplet 142, 242 to a testing structure, such as the droplet cup 140, 240. In the shown examples there are five reagent containers 132, 232 that may include cleaning and/or testing reagents such as de-ionized (DI) water, hydrogen fluoride (HF), hydrogen peroxide ($H_2O_2$), hydrogen chloride (HCl), nitric acid ($HNO_3$), varying combinations and/or concentrations of the aforementioned exemplary cleaning and/or testing reagents, and/or any cleaning and/or testing reagents known or yet to be discovered. In practice, the liquid transfer pipette arm 130, 230 may, for example, first be cleaned in a reagent container 132, 232 (that includes DI water or another cleaning reagent for cleaning the tip of the liquid transfer pipette arm 130, 230 between uses) and then pick up one or more testing reagents from one or more additional reagent container 132, 232. The picked up testing reagent on the tip of the liquid transfer pipette arm 130, 230 would then be transferred to the testing structure (e.g. the droplet cup 140, 240).

During contaminant testing of the wafer 150, 250 there is relative movement between the wafer 150, 250 and the droplet cup 140, 240 (and the tip well 144, 244 of the droplet cup 140, 240). Although the droplet of testing reagent 142, 242 skims the surface of the wafer 150, 250, it substantially stays within the tip well 144, 244 of the droplet cup 140, 240 although at least part of the droplet 142, 242 is above the uppermost surface of the tip of the droplet cup 140, 240. This may be accomplished by, for example, surface tension, gravity, and/or momentum (spinning). For example, because the droplet surface area that contacts the tip well 144, 244 is greater than the droplet surface area that contacts the wafer 150, 250, the droplet 142, 242 remains in the tip well 144, 244 during contamination scanning. In addition, because the shown droplet cup 140, 240 is below the wafer 150, 250, the droplet of testing reagent 142, 242 within the tip well 144, 244 would be pulled by gravity towards the tip well 144, 244. Finally, the spinning of the droplet cup 140, 240 (and the tip well 144, 244 of the droplet cup 140, 240) would provide momentum that would make the droplet of testing reagent 142, 242 tend to continue in the same direction of the spinning droplet cup 140, 240 as opposed to changing directions to follow the wafer 150, 250. Surface tension, gravity, and momentum may work alone or in combination with each other such that the droplet of testing reagent 142, 242 substantially stays within the tip well 144, 244 of the droplet cup 140, 240.

Then, after scanning, the liquid transfer pipette arm 130, 230 recovers the droplet of testing reagent 142, 242 (now possibly including contaminants from the wafer 150, 250) from the testing structure and transfers it to the analysis structure. Prior to recovering the contaminated droplet, the liquid transfer pipette arm 130, 230 may be cleaned (e.g. in a shown reagent container 132, 232 or a different reagent container containing DI water or another cleaning reagent). The liquid transfer pipette arm 130, 230 then carries the droplet used in the scanning process to the analysis structure represented as at least one sample tray 160, 260. In practice, collection vials (not shown) may be held in the tray 160, 260. A separate mechanism, showed as an arm 162, 262 may be used to open and close the vial caps or lids of the collection vials. Specifically, the arm 162, 262 may remove a cap from a vial just prior to the transfer of the contaminated droplet to the vial. After the transfer of the contaminated droplet, the arm 162, 262 may replace the cap on the vial to protect the contaminated droplet from being contaminated by a source other than the wafer currently being tested. Alternative mechanisms and methods (including manual mechanisms and methods) may be used to transfer the contaminated droplet from the testing structure and transfer it to the analysis structure.

Although shown as a single liquid transfer pipette arm 130, 230, alternatively, a first liquid transfer pipette arm could be used for transferring the liquid to the testing structure and a second transfer pipette arm could be used for transferring the liquid from the testing structure to the analysis structure. In another alternative example, multiple liquid transfer pipette arms could be used for either or both of these steps. The liquid transfer pipette arm 130, 230 may extend through the table 112, 212 and be pivoted between multiple positions (shown as swinging about an axis) by the internal workings 110, 210 such as one or more of a suitable mechanical structure, a hydraulic structure, a pneumatic structure, a manual structure, and/or other movement means known or yet to be discovered.

Finally, after collection of one or more droplets (some of which may contain contaminants) in the vials held in the sample tray 160, 260, the one or more droplets may be analyzed for the presence and/or quantity of contaminants. For example, the samples may be analyzed via inductively coupled plasma mass spectrometry (ICP-MS). Various devices for performing ICP-MS are described in U.S. Pat. Nos. 7,619,213, 7,488,925, and 7,473,893, which are herein incorporated by reference. Another exemplary method for analyzing the sample would be Total Reflections X-ray Fluorescence (TXRF). Various devices for performing TXRF are described in U.S. Pat. Nos. 5,866,899, 5,930,586, and 6,043,486, which are herein incorporated by reference. It will be appreciated that any other analysis method known or yet to be discovered may be used in association with the above described scanners.

Horizontal Scanner(s):

FIGS. 1, 2, 3, 4, 5A, and 5B show an exemplary horizontal scanner 100 (or the horizontal configuration of a dual-configuration scanner) or portions thereof. The horizontal scanner 100 is able to scan the wafer 150 while it is in a horizontal orientation (parallel to the table 112). The overview above provides many of the details that may be incorporated in this more specific description, but have been omitted to avoid redundancy.

As shown in FIG. 2, the wafer 150 may be manually or automatically loaded onto (associated with) the wafer axel 121 when the horizontal scanner 100 is in the wafer-loading (or unloading) position. In the shown exemplary wafer-loading position, the wafer lift shaft 124 has been raised and, in turn, the wafer support arm 122 has been raised. This allows easy access to the wafer axel 121 for the purpose of mounting (associating) the wafer 150.

Prior to, at the same time, or shortly after the loading of the wafer 150, the liquid transfer pipette arm 130 may pivot (or otherwise move between) the reagent containers 132 (for cleaning and obtaining a droplet of testing reagent 142) and the tip well 144 of the droplet cup 140 (into which the liquid transfer pipette arm 130 deposits the droplet 142). Specifically, the tip of the liquid transfer pipette arm 130 is inserted into a first reagent container 132 for cleaning and then inserted into at least one reagent container 132 to obtain the droplet 142. The liquid transfer pipette arm 130 then pivots to deposit the droplet 142 in the tip well 144 of the droplet cup 140. The position of the droplet cup 140 may be adjusted to be accessible to the liquid transfer pipette arm 130.

FIG. 3 shows the scanner 100 in the contaminant-testing position. In the shown exemplary contaminant-testing position, the wafer lift shaft 124 has been lowered and, in turn, the wafer support arm 122 has been lowered. The droplet cup 140 is not visible in this figure because it has been moved into testing position beneath the wafer 150. The peripheral edge 154 of wafer 150 may be proximal to, abutted to, or just above at least part of the alignment pegs 125. The top surfaces of alignment pegs 125 are shown as being slanted toward the wafer, thereby providing a surface that may contact both the lower surface 152 and the beveled edge 154 of the wafer 150. The actual height location of the wafer 150 would be above the uppermost surface of the droplet cup 140, but low enough so that the upper surface (top) of droplet 142 contacts the lower surface 152 of the wafer 150. It should be noted that the surface tension properties of the droplet 142 in the droplet cup 140 allow the droplet 142 to sit in a concave tip well so that at least part of the droplet 142 is above the uppermost surface of the tip of the droplet cup 140. Because at least part of the droplet 142 is above the uppermost surface of the tip of the droplet cup 140, the droplet 142 can make contact with the lower surface 152 of a horizontally-oriented wafer 150 without the lower surface 152 of the horizontally-oriented wafer 150 coming into contact with the droplet cup 140 itself.

Figure 4A:
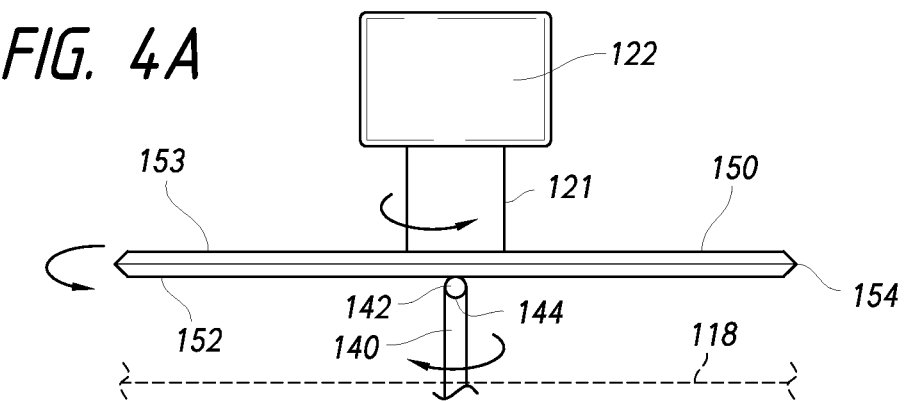
FIGS. 4A-4C are a series of side views of the exemplary horizontal scanner of FIG. 1, showing the relative movement between the droplet and the wafer and, more specifically, the rotational movement of the wafer and the lateral and rotational movement of the droplet cup.
Figure 4B:
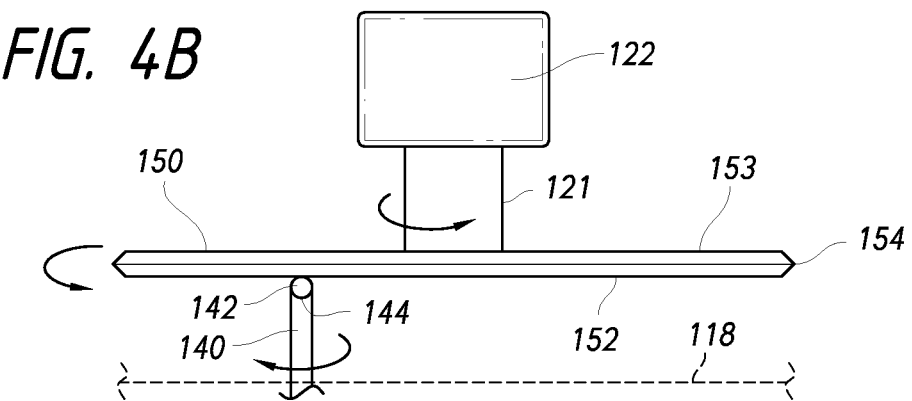
Figure 4C:
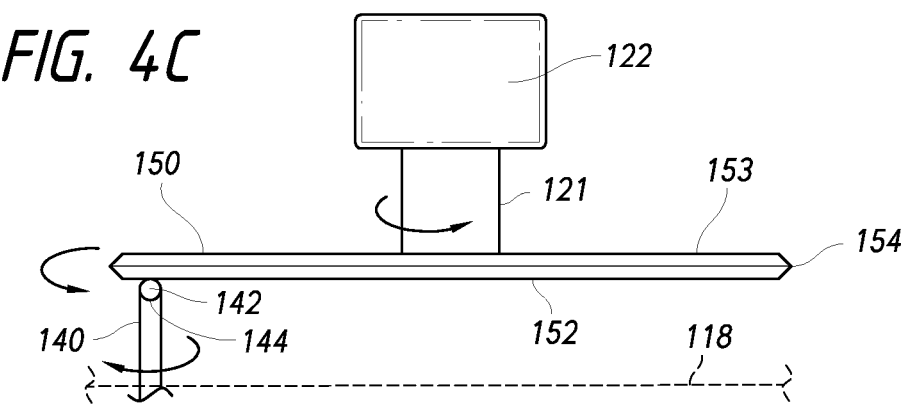

FIGS. 4A-4C show a progression of views of the droplet cup 140 and the wafer 150 in an exemplary contaminant-testing position. The progression of these three figures show the droplet cup 140 moving or traveling (adjusting) along the length of the slot 118 (lateral movement) with the top of the droplet of testing reagent 142 skimming or scanning the lower surface 152 of the wafer 150 and gathering contaminants (if present) therefrom. The shown slot 118 extends substantially the length of the diameter of the wafer 150, and perhaps beyond. It should be noted, however, that the slot 118 may be the length of the radius of the wafer 150, starting from the center of the wafer 150 and extending a bit beyond the outer periphery of the wafer 150. Although the progression of FIG. 4A to FIG. 4C shows the droplet cup 140 moving from the center of the wafer 150 to the outer periphery of the wafer 150, an alternative progression could be from FIG. 4C to FIG. 4A, where the droplet cup 140 moves from the outer periphery of the wafer 150 to the center of the wafer 150.

In addition to lateral movement, FIGS. 4A-4C show that the droplet cup 140 being rotated (either in a clockwise direction or a counter-clockwise direction) while the wafer axel 121 and the wafer 150 are rotated in the opposite direction (either in the counter-clockwise direction or the clockwise direction). It will be appreciated that in alternate examples, the droplet cup 140, the wafer axel 121, and the wafer 150 are all rotated in the same direction (clockwise or counter-clockwise). It will be appreciated that the droplet cup 140 may not rotate (remain stationary) while the wafer axel 121 and the wafer 150 rotates in either a clockwise direction or a counter-clockwise direction.

During contaminant testing of the wafer 150, the combination of the lateral movement of the droplet cup 140 and the rotation of the wafer 150 results in a spiral movement relationship between the wafer 150 and the top of the droplet of testing reagent 142. FIG. 5A shows the progression of FIG. 4A to FIG. 4C, in which the droplet cup 140 starts at the center of the lower surface 152 of the wafer 150 and moves towards the outer periphery of the lower surface 152 of the wafer 150, resulting in a spiral that starts from the center of the lower surface 152 of the wafer 150 and spirals outward. FIG. 5B shows the progression of FIG. 4C to FIG. 4A, in which the droplet cup 140 starts at the outer periphery of the lower surface 152 of the wafer 150 and moves towards the center of the lower surface 152 of the wafer 150, resulting in a spiral that starts from the outer periphery of the lower surface 152 of the wafer 150 and spirals inward. The spiral patterns have the advantage of being able to substantially cover the entire lower surface 152 of the wafer 150 and thus the scanning process covers substantially the entire lower surface 152 of the wafer 150. It should be noted that the shown spiral patterns are exemplary and that actual spiral patterns may have more or less space between successive iterations of the spiral path. (The spacing of the spiral path would be controlled by relative rates of the rotation of the wafer 150 and the lateral movement of the droplet cup 140.) It should also be noted that alternative patterns are possible in which the relative movement between the droplet 142 and the lower surface 152 of the wafer 150 is different.

During contaminant testing, the top of the droplet of testing reagent 142 is skimmed along the lower surface 152 of the wafer 150 and contaminants (if any) are at least partially diffused or otherwise transferred into the droplet of testing reagent 142. Then, as set forth in the overview, the liquid transfer pipette arm 130 recovers the droplet of testing reagent 142 (now possibly including contaminants from the wafer 150) from the testing structure and transfers it to the analysis structure.

A computer (not shown) with appropriate software, hardware, and/or firmware may be used for controlling components of the scanner 100 including, but not limited to the wafer axel 121 (e.g. rotation), the wafer support arm 122, the support/lift interconnection 123, the wafer lift shaft 124 (e.g. raising and lowering), the liquid transfer pipette arm 130 (e.g. up and down movements and pivoting between other components), the droplet cup 140 (e.g. rotation and lateral movement), the wafer 150 (e.g. loading, unloading, and rotation). The control may be related to positioning, rates (e.g. rates of rotation, pivoting, and/or movement), direction (e.g. directions of rotation, pivoting, and/or movement), and other variables of the components.

Vertical Scanner(s):

FIGS. 6-8 show an exemplary vertical scanner 200 (or the vertical configuration of a dual-configuration scanner) or portions thereof. The vertical scanner 200 is able to scan the wafer 250 while it is in a vertical orientation (perpendicular to the table 212). The overview above provides many of the details that may be incorporated in this more specific description, but have been omitted to avoid redundancy. In FIGS. 6-8 the slot 218 is shown in phantom. For a vertical scanner 200 the slot 218 that allows for lateral movement of the droplet cup 240 would be optional.

It should be noted that the slot 218 in a vertical scanner 200 might be included to allow the droplet cup 240 to be adjusted. The slot 218 might be helpful for allowing the droplet cup 240 to be adjusted to load the wafer 250, to unload the wafer 250, or to position the droplet cup 240 for easier access by the liquid transfer pipette arm 230 during the deposit of the droplet 242. Similarly, the alignment pegs 225 are optional in a vertical scanner 200. It should be noted, however, that if the scanner 200 is a dual-configuration scanner 100, 200, then both the slot 118, 218 and the alignment pegs 125, 225 would be present for when the dual-configuration scanner 100, 200 is used as a horizontal scanner for scanning the wafer 150, 250 in a horizontal orientation.

As shown in FIG. 7, the wafer 250 may be manually or automatically loaded onto (associated with) the wafer axel 221 (not shown) when the vertical scanner 200 is in the wafer-loading (or unloading) position. In the shown exemplary wafer-loading position, the wafer lift shaft 224 has been raised and, in turn, the wafer support arm 222 has been raised. This allows easy access to the wafer axel 221 for the purpose of mounting (associating) the wafer 250.

Prior to, at the same time, or shortly after the loading of the wafer 250, the liquid transfer pipette arm 230 may pivot (or otherwise move between) the reagent containers 232 (for cleaning and obtaining a droplet of testing reagent 242) and the tip well 244 of the droplet cup 240 (into which the liquid transfer pipette arm 230 deposits the droplet 242). Specifically, the tip of the liquid transfer pipette arm 230 is inserted into a first reagent container 232 for cleaning and then inserted into at least one reagent container 232 to obtain the droplet 242. The liquid transfer pipette arm 230 then pivots to deposit the droplet 242 in the tip well 244 of the droplet cup 240. The position of the droplet cup 240 may be adjusted to be accessible to the liquid transfer pipette arm 230.

FIG. 8 shows the scanner 200 in the contaminant-testing position. In the shown exemplary wafer-loading position, the wafer lift shaft 224 has been lowered and, in turn, the wafer support arm 222 has been lowered. The bottom of the peripheral edge 254 of the wafer 250 is adjusted so that it would be above the uppermost surface of the droplet cup 240, but low enough so that the upper surface of droplet 242 contacts the bottom of the peripheral edge 254 of the wafer 250. The wafer 250 is rotated (clockwise or counterclockwise) so that at least a substantial portion of the peripheral edge 254 of the wafer 250 rotates through the droplet of testing reagent 242. The droplet cup 240 may rotate (clockwise or counterclockwise) or be stationary. When the bottom of the peripheral edge 254 of the rotating wafer 250 comes in contact with the top of the droplet of testing reagent 242 the droplet 242 contaminants (if present) may be diffused or otherwise transferred from the peripheral edge 254 of the wafer 250 into the droplet 242. It should be noted that the "bottom of the peripheral edge 254" (also referred to as the "beveled edge 254") that comes into contact with the droplet of testing reagent 242 may include the extreme outer edge, the beveled surfaces, and a small portion (the outer periphery) of the lower surface 252 and/or the upper surface 251 of the wafer 250.

Figure 9:
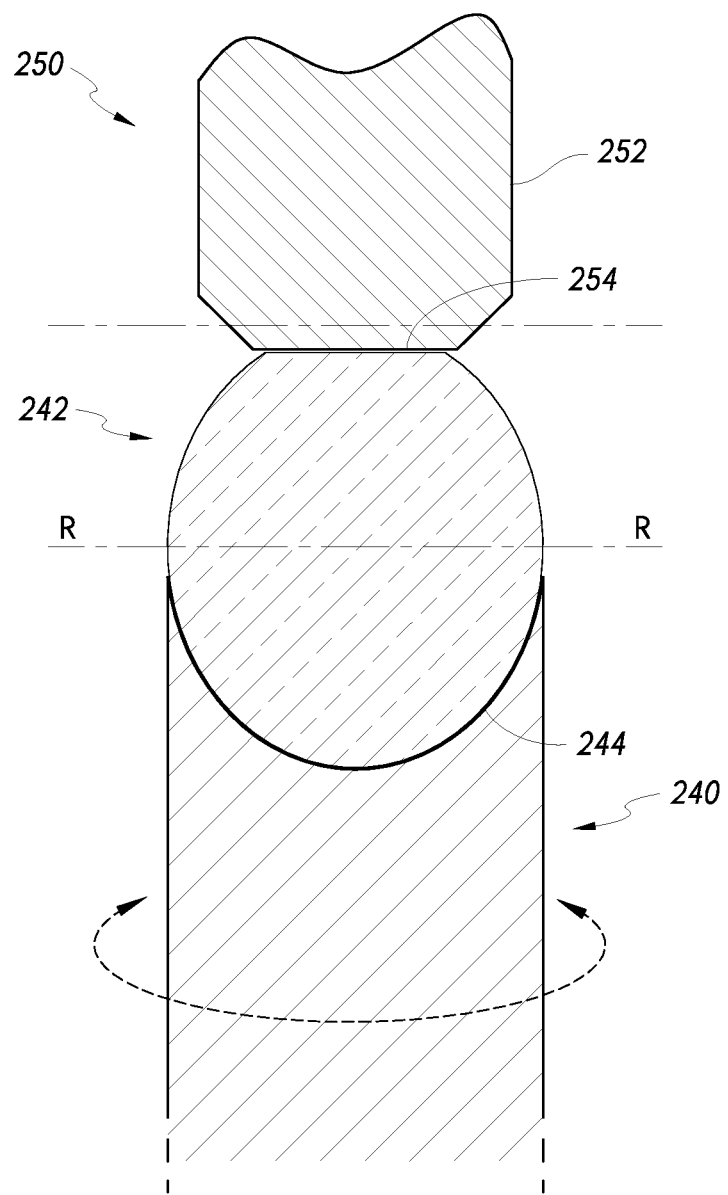
FIG. 9 is a cross-sectional view of an exemplary tip well of a droplet cup having a droplet therein and a bottom portion of the peripheral edge of a wafer contacting at least part of the droplet above the uppermost portion of the tip well.

FIG. 9 shows a detailed cross-sectional view of an exemplary droplet cup 240 (having a tip well 244), a droplet of testing reagent 242, and a bottom peripheral edge 254 of a wafer 250. Reference line R-R is an imaginary dividing line that distinguishes a lower portion of the droplet 242 (that is disposed within the tip well 244) from an upper portion of the droplet 242 (that is disposed above the tip well 244). The beveled edge 254 is shown as being in contact (skimming) with the upper portion of the droplet 242. The surface area of the tip well 244 that is in contact with the droplet 242 is preferably greater than the surface area of the portion of the wafer 250 that contacts the droplet 240 (e.g. the bottom of the peripheral edge 254). Accordingly, during contaminant testing, the droplet 242 has greater adherence to the tip well than either lower surface 152 or beveled edge 254. Therefore, the droplet may remain in the tip well, even during contamination testing of a hydrophilic (or hydrophobic) wafer 250 when the beveled edge 254 skims the upper portion of the droplet 242.

During contaminant testing, the beveled edge 254 of the wafer 250 is skimmed by the top of the droplet of testing reagent 242 and contaminants (if any) are at least partially diffused or otherwise transferred into the droplet of testing reagent 242. Then, as set forth in the overview, the liquid transfer pipette arm 230 recovers the droplet of testing reagent 242 (now possibly including contaminants from the wafer 250) from the testing structure and transfers it to the analysis structure.

A computer (not shown) with appropriate software, hardware, and/or firmware may be used for controlling components of the scanner 200 including, but not limited to the wafer axel 221 (e.g. rotation), the wafer support arm 222, the support/lift interconnection 223, the wafer lift shaft 224 (e.g. raising and lowering), the liquid transfer pipette arm 230 (e.g. up and down movements and the pivoting between other components), the droplet cup 240 (e.g. rotation and lateral movement), the wafer 250 (e.g. loading, unloading, and rotation). The control may be related to positioning, rates (e.g. rates of rotation, pivoting, and/or movement), direction (e.g. directions of rotation, pivoting, and/or movement), and other variables of the components.

Alternative Droplet Cups:

FIGS. 10A-10I show cross-sectional views of alternative droplet cup tips 300a-i of the droplet cups 140, 240 of the scanners 100, 200. Each of the alternative droplet cup tips 300a-i is suitable for holding a droplet of testing reagent 302a-i in a concave tip well 304a-i. These exemplary alternative droplet cup tips 300a-i are meant to be exemplary and are not meant to be limiting.

Figures 10A, 10B, 10C:
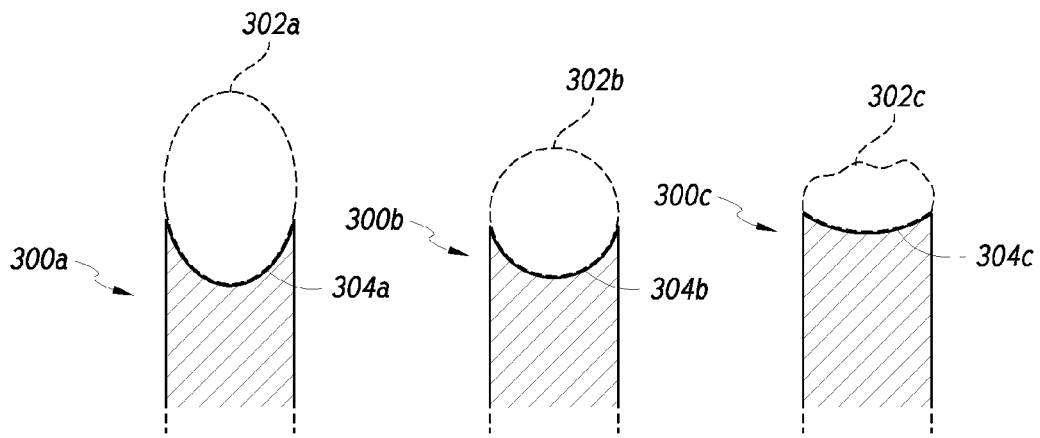
FIGS. 10A-10I are cross-sectional views of alternative droplet cup tips that may be used with any of the shown or described scanners.

As shown in FIGS. 10A-10C, tip wells 304a-c of the droplet cup tips 300a-c may have an at least substantially continuously curving concave surface. In cross-section this is shown as the tip wells 304a-c being a continuous arc from a first side of the droplet cup tip 330a-c to a second side of the droplet cup tip 330a-c. For example, the shown tip wells 304a-c may be have a deep depth (as shown in 330a), an intermediate depth (as shown in 330b), or a shallow depth (as shown in 330c).

Figures 10D, 10E, 10F:
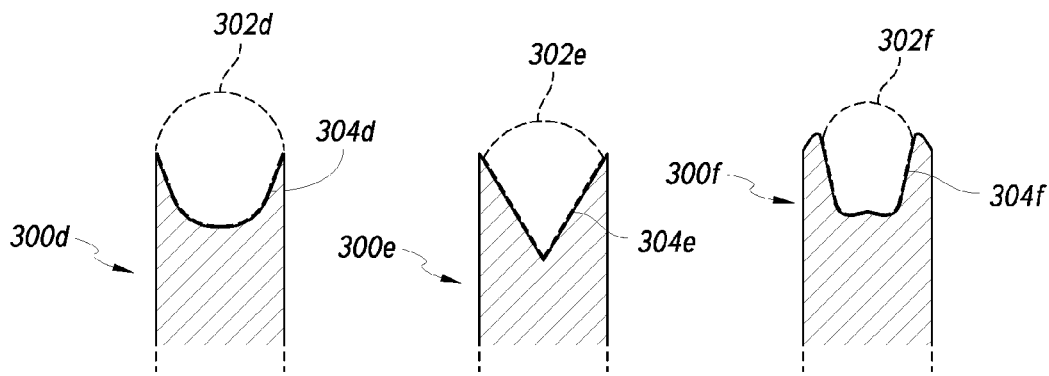

As shown in FIGS. 10D-10F, tip wells 304d-f of the droplet cup tips 300d-f may have a discontinuously concave surface. In cross-section this is shown as the tip wells 304d-f being discontinuous from a first side of the droplet cup tip 330d-f to a second side of the droplet cup tip 330d-f. For example, the shown tip wells 304d-f may have cross-sections that have a "U" shape (as shown in 330d), a "V" shape (as shown in 330e), or a bottom that is flat, irregular, or slightly convex (as shown in 330f). Although not shown, the tip well could also be cylindrical with a flat bottom.

As shown in FIG. 10F, the tip well 304f of the droplet cup tip 300f may not extend to the absolute outer peripheral edge of the droplet cup tip 300f. In this shown droplet cup tip 300f, at least a portion of the rim surrounding the tip well 304f is higher than the absolute outer peripheral edge of the droplet cup tip 300f. This configuration might be applied to other droplet cup tips including, but not limited to those shown in FIGS. 10A-E and FIGS. 10G-1.

Figures 10G, 10H, 10I:
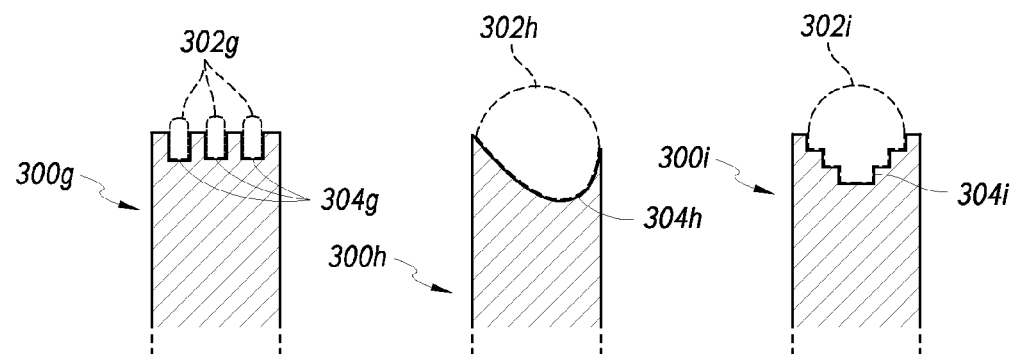

As shown in FIG. 10G, the droplet cup tip 300g may include a plurality of the tip wells 304g. In this shown droplet cup tip 300g, each of the tip wells 304g has a flat bottom. Alternatively, each the bottom of the tip wells 304g may have shapes similar to those shown in FIGS. 10A-F and FIGS. 10H-1. It should be noted that, although shown as three tip wells 304g, FIG. 10G is meant to show any plurality of tip wells 304g.

As shown in FIG. 10H, the tip well 304h of the droplet cup tip 300h may be asymmetrical. This might be practical if having a steeper incline on the side of the cup tip 300h towards which the wafer is rotating would to help keep the droplet 302h within the tip well 304h. This configuration might be applied to other droplet cup tips including, but not limited to those shown in FIGS. 10A-G and FIG. 10I. For example, the point of the "V" shaped tip well 304e in FIG. 10E may not be positioned centrally.

As shown in FIG. 10I, the tip well 304i of the droplet cup tip 300i may be a non-curved tip well 304i. As shown, the cross-section of the tip well 304i has a stepped configuration and may provide greater surface area for adhesion of the droplet 302i to the tip well 304i.

Alternative Alignment Pegs:

As set forth herein, alignment pegs 125, 225 may be used as part of the wafer positioning and rotating structures. Alignment pegs 125, 225 may be used to assist in the positioning of the wafer 150, 250 when it is in the horizontal orientation. As shown, the peripheral edge 154 of a horizontally positioned wafer 150 may be proximal to, abutted to, or just above at least part of the alignment pegs 125. The top surfaces of alignment pegs 125 are shown as being slanted toward the wafer, thereby providing a surface that may contact both the lower surface 152 and the beveled edge 154 of the horizontally positioned wafer 150.

Figure 12:
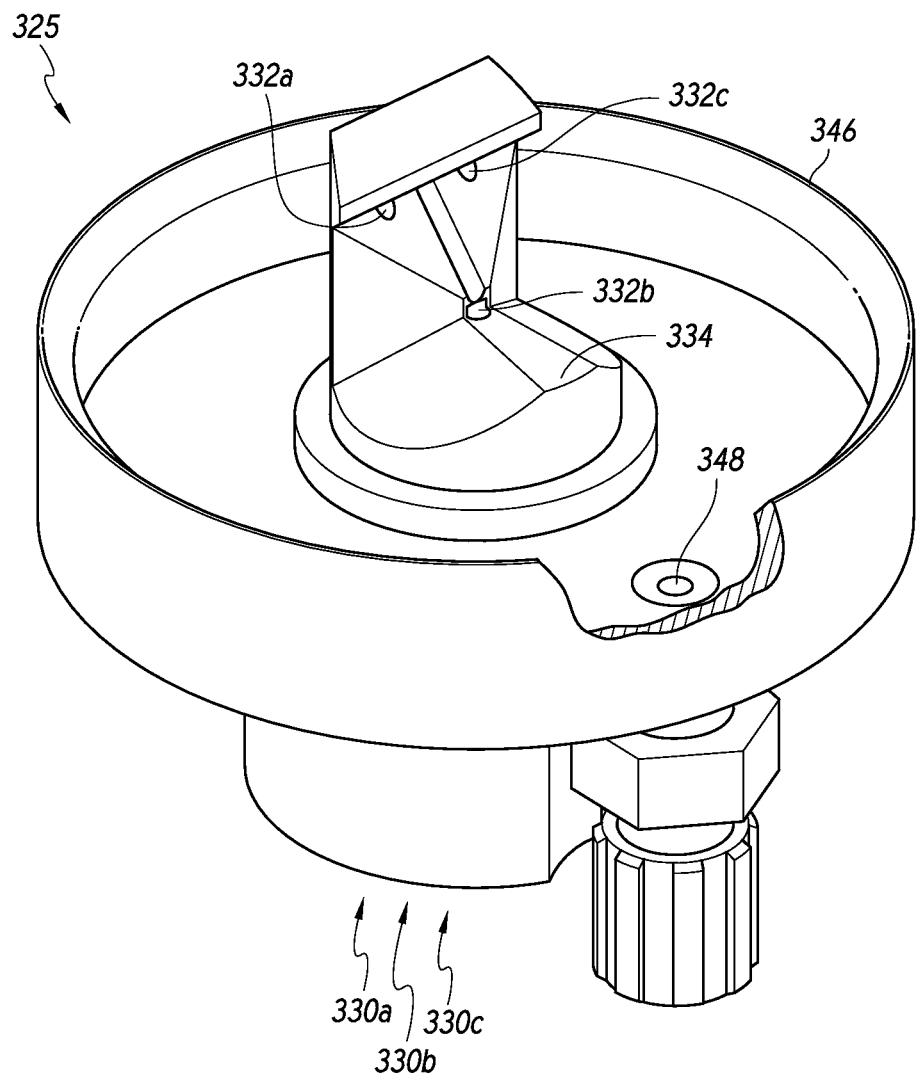
FIG. 12 is a perspective view of an alternative exemplary alignment peg that is self-cleaning.

FIG. 12 is a perspective view of an alternative exemplary alignment peg 325 that is self-cleaning and/or self-sterilizing. This alignment peg can replace the alignment pegs 125, 225 shown in the other figures. In general, a self-cleaning and/or self-sterilizing alignment peg 325 could use cleaning/sterilizing methods including, but not limited to rinsing (using, for example, a chemical or gas rinse), heating, ionization, ultrasonication, vacuum, laser, sputtering, dry etching, and/or any other cleaning/sterilizing means known or yet to be discovered. The shown alignment peg 325 uses rinsing technology in which at least one cleaning/sterilizing chemical or gas (e.g. de-ionized (DI) water) are transmitted via at least one passageway 330a-c (shown as coming from below the alignment peg 325) to one or more apertures 332a-c. The alignment peg 325 has a wafer support surface 334 upon which the wafer is supported. It is this wafer support surface 334 that should be clean and/or sterile. Accordingly, the apertures 332a-c are positioned so that the cleaning/sterilizing chemical or gas is directed towards the wafer support surface 334. If the cleaning/sterilizing chemical or gas is a liquid or fluid, the alignment peg 325 would preferably include structure to "catch" the cleaning/sterilizing chemical or gas. To this end, the shown alignment peg 325 includes a peripheral wall 346 and a drain 348. The wafer support surface 334 may be slightly angled (e.g. 1%-15%) downwards or towards the drain 348 to direct fluid thereto. Also, the wafer support surface 334 should be positioned so that the wall 346 does not interfere (e.g. is below) with the wafer support surface's function of supporting the wafer.

Alternative features that may be incorporated in one or more of the shown alignment pegs 125, 225, and/or alternative alignment pegs 325 include, but are not limited to the following:

A retractable feature such that the alignment peg(s) may be retracted partially or completely below the table 112, 212;

A sheath that may be removable and/or retractable from the alignment peg(s), the sheath being using used for physical protection or protection from contamination;

An adjustable feature such that the alignment peg(s) may be adjusted to accommodate different sizes and types of wafers;

A replaceable feature such that the alignment peg(s) may be replaced (e.g. with alternative alignment peg(s) or to replace one or more broken or contaminated alignment peg(s));

A microscope associated at or near where the alignment peg contacts the wafer so that the surface of the wafer can be examined; and/or A camera associated at or near where the alignment peg contacts the wafer so that the surface of the wafer may be photographed, videoed, or otherwise imaged or viewed remotely.

Methods:

As set forth above, although not specifically shown, appropriate software, hardware, and/or firmware may be used for controlling the scanners (including the internal workings 110, 210 and/or the applied workings 120, 220). Exemplary methods may include steps, actions, and/or functions associated with controlling the wafer axel 121, 221 (e.g. rotation), the wafer support arm 122, 222, the support/lift interconnection 123, 223, the wafer lift shaft 124, 224 (e.g. raising and lowering), the liquid transfer pipette arm 130, 230 (e.g. up and down movements and the pivoting between other components), the droplet cup 140, 240 (e.g. rotation and lateral movement), the wafer 150, 250 (e.g. loading, unloading, and rotation). The control may be related to positioning, rates (e.g. rates of rotation, pivoting, and/or movement), direction (e.g. directions of rotation, pivoting, and/or movement), and other variables of the components. Exemplary methods may include steps, actions, and/or functions associated with the scanning in the horizontal and/or vertical orientations.

The methods disclosed herein include one or more steps, actions, and/or functions for achieving the described actions and results. The method steps, actions, and/or functions may be interchanged with one another without departing from the scope of the present invention. In other words, unless a specific order of steps, actions, and/or functions is required for proper operation of the exemplary scanners, the order and/or use of specific steps, actions, and/or functions may be modified without departing from the scope of the present invention.

The steps, actions, and/or functions of the methods may be controlled using one or more computers that are controlled by one or more programs (or subprograms thereof). The computers, in turn, control the scanners or components thereof using "signals" (which may any type of appropriate communication and/or transmissions). Signals transmitted from (or otherwise obtained from) the computer and received (or otherwise obtained) by the scanners or components thereof cause the scanners or components thereof to implement the appropriate steps, actions, and/or functions of the methods.

Exemplary computers include at least one associated "processing unit" and at least one associated "memory." A processing unit may be a processor (or other processing device known or yet to be discovered) that is capable of implementing steps or actions or directing (directly or indirectly) other components to implement steps or actions. Memory is any computer-readable storage media including non-transitory memory (e.g. RAM memory, flash memory, ROM memory, EPROM memory, EEPROM memory, registers, hard disk, a removable disk, a CD-ROM, a USB drive, or any other form of storage media means known or yet to be discovered).

It is to be understood that the inventions, examples, and embodiments described herein are not limited to particularly exemplified materials, methods, and/or structures. It is to be understood that the inventions, examples, and embodiments described herein are to be considered preferred inventions, examples, and embodiments whether specifically identified as such or not.

All references (including, but not limited to, foreign and/or domestic publications, patents, and patent applications) cited herein, whether supra or infra, are hereby incorporated by reference in their entirety.

The terms and expressions that have been employed in the foregoing specification are used as terms of description and not of limitation, and are not intended to exclude equivalents of the features shown and described. While the above is a complete description of selected embodiments of the present invention, it is possible to practice the invention use various alternatives, modifications, adaptations, variations, and/or combinations and their equivalents. It will be appreciated by those of ordinary skill in the art that any arrangement that is calculated to achieve the same purpose may be substituted for the specific embodiment shown. It is also to be understood that the following claims are intended to cover all of the generic and specific features of the invention herein described and all statements of the scope of the invention that, as a matter of language, might be said to fall therebetween.

What is claimed is:

1. A scanner for scanning at least one wafer having an upper surface, a lower surface, and a peripheral edge, said scanner comprising:
    (a) a droplet cup with a droplet cup tip, said droplet cup tip having a concave tip well with an uppermost surface, said tip well configured to hold a droplet of testing reagent so that at least part of said droplet is above said uppermost surface of said droplet cup tip; and
    (b) wafer positioning and rotating structure configured to position said wafer above said droplet cup tip such that at least part of said wafer contacts said at least part of said droplet above said uppermost surface of said droplet cup tip;
    (c) wherein there is relative movement between said droplet and said wafer during a scanning process.

2. The scanner of claim 1, wherein surface tension causes said at least part of said droplet to be held above said uppermost surface of said droplet cup tip.

3. The scanner of claim 1, said scanner being a dual-configuration scanner that converts between a horizontal scanner for scanning said lower surface of said wafer and a vertical scanner for scanning said peripheral edge of said wafer.

4. The scanner of claim 1, said scanner being a horizontal scanner for scanning said lower surface of said wafer in a horizontal orientation.

5. The scanner of claim 1, said scanner being a vertical scanner for scanning said peripheral edge of said wafer in a vertical orientation.

6. The scanner of claim 1, said scanner being a horizontal scanner for scanning said lower surface of said wafer in a horizontal orientation, and said relative movement between said droplet and said wafer creates a pattern therebetween.

7. The scanner of claim 1, said scanner further comprising at least one liquid transfer structure for transferring said droplet of testing reagent from at least one reagent container to said tip well.

8. The scanner of claim 1, said scanner including at least one alignment peg for aligning said wafer in a horizontal orientation.

9. The scanner of claim 1, said scanner including at least one self-cleaning or self-sterilizing alignment peg for aligning said wafer in a horizontal orientation.

10. The scanner of claim 1, said scanner including at least one self-cleaning or self-sterilizing alignment peg for aligning said wafer in a horizontal orientation, said at least one self-cleaning alignment peg being selected from the group consisting of:
    (a) at least one self-cleaning alignment peg having at least one wafer support surface that may be cleaned or sterilized by rinsing;
    (b) at least one self-cleaning alignment peg having at least one wafer support surface that may be cleaned or sterilized by heating;
    (c) at least one self-cleaning alignment peg having at least one wafer support surface that may be cleaned or sterilized by ionization;
    (d) at least one self-cleaning alignment peg having at least one wafer support surface that may be cleaned or sterilized by ultrasonication;
    (e) at least one self-cleaning alignment peg having at least one wafer support surface that may be cleaned or sterilized by vacuum;
    (f) at least one self-cleaning alignment peg having at least one wafer support surface that may be cleaned or sterilized by laser;
    (g) at least one self-cleaning alignment peg having at least one wafer support surface that may be cleaned or sterilized by sputtering; and
    (h) at least one self-cleaning alignment peg having at least one wafer support surface that may be cleaned or sterilized by dry etching.

11. A scanner for scanning at least one wafer having an upper surface, a lower surface, and a peripheral edge, said scanner comprising:
    (a) a single droplet of testing reagent; and
    (b) wafer positioning and rotating structure configured to position a wafer in a horizontal orientation above said single droplet such that at least part of said lower surface of said wafer contacts at least part of said droplet;
    (c) wherein there is relative movement between said single droplet and said wafer during a scanning process.

12. The scanner of claim 11, said single droplet of testing reagent positioned within a tip well of a droplet cup tip of a droplet cup, said tip well having an uppermost surface, said single droplet of testing reagent positioned within said tip well such that at least part of said single droplet is above said uppermost surface of said droplet cup tip, at least part of the lower surface of said wafer contacting said at least part of said single droplet above said uppermost surface.

13. The scanner of claim 11, said scanner being a dual-configuration scanner in which said wafer positioning and rotating structure transitions between positioning said wafer in said horizontal orientation and positioning said wafer in a vertical orientation for scanning said peripheral edge of said wafer.

14. The scanner of claim 11, said relative movement between said single droplet and said wafer creating a pattern therebetween.

15. The scanner of claim 11, said scanner further comprising at least one liquid transfer structure for transferring said single droplet of testing reagent from at least one reagent container to said tip well.

16. The scanner of claim 11, said scanner including at least one self-cleaning or self-sterilizing alignment peg for aligning said wafer.

17. A dual-configuration scanner for scanning at least one wafer having an upper surface, a lower surface, and a peripheral edge, said dual-configuration scanner comprising:
    (a) testing reagent; and
    (b) wafer positioning and rotating structure for positioning a wafer above said testing reagent such that at least part of said wafer contacts at least part of said testing reagent;
    (c) said wafer positioning and rotating structure further for transitioning said wafer between a horizontal orientation and a vertical orientation;
    (d) said wafer positioning and rotating structure rotating said wafer in said horizontal orientation such that there is relative movement between said testing reagent and the lower surface said wafer during a scanning process; and
    (e) said wafer positioning and rotating structure rotating said wafer in said vertical orientation such that there is relative movement between said testing reagent and the peripheral edge said wafer during a scanning process.

18. The dual-configuration scanner of claim 17:
    (a) said testing reagent being a droplet of testing reagent; and
    (b) said wafer positioning and rotating structure for positioning said wafer above said droplet of testing reagent such that at least part of said wafer contacts the top of said droplet of testing reagent;
    (c) said wafer positioning and rotating structure rotating said wafer in said horizontal orientation such that there is relative movement between the top of said droplet of testing reagent and the lower surface said wafer during a scanning process; and
    (d) said wafer positioning and rotating structure rotating said wafer in said vertical orientation such that there is relative movement between the top of said droplet of testing reagent and the peripheral edge said wafer during a scanning process.

19. The dual-configuration scanner of claim 17:
    (a) said testing reagent being a droplet of testing reagent within a tip well of a droplet cup tip of a droplet cup, said tip well having an uppermost surface, said droplet of testing reagent positioned within said tip well such that at least part of said droplet is above said uppermost surface of said droplet cup tip; and
    (b) said wafer positioning and rotating structure for positioning said wafer above said droplet of testing reagent such that at least part of said wafer contacts the at least part of said droplet above said uppermost surface of said droplet cup tip;
    (c) said wafer positioning and rotating structure rotating said wafer in said horizontal orientation such that there is relative movement between the at least part of said droplet above said uppermost surface of said droplet cup tip and the lower surface said wafer during a scanning process; and
    (d) said wafer positioning and rotating structure rotating said wafer in said vertical orientation such that there is relative movement between the at least part of said droplet above said uppermost surface of said droplet cup tip and the peripheral edge said wafer during a scanning process.

20. The scanner of claim 1, further comprising:
    (a) said concave tip well having a surface area contacting said droplet;
    (b) a portion of said wafer contacting said droplet having a surface area; and
    (c) said surface area of said concave tip well contacting said droplet being larger than said surface area portion of said wafer contacting said droplet so that said droplet has greater adherence to said concave tip well than to said portion of said wafer contacting said droplet.

21. The scanner of claim 11, further comprising:
    (a) said single droplet of testing reagent positioned within a tip well of a droplet cup tip of a droplet cup;
    (b) said tip well having a surface area contacting said single droplet, a portion of said wafer contacting said single droplet having a surface area; and
    (c) said surface area of said tip well contacting said single droplet being larger than said surface area portion of said wafer contacting said single droplet so that said single droplet has greater adherence to said tip well than to said portion of said wafer contacting said single droplet.

22. The dual-configuration scanner of claim 17, further comprising:
    (a) said testing reagent being a droplet of testing reagent within a tip well of a droplet cup tip of a droplet cup;
    (b) said tip well having a surface area contacting said droplet, a portion of said wafer contacting said droplet having a surface area; and
    (c) said surface area of said tip well contacting said droplet being larger than said surface area portion of said wafer contacting said droplet so that said droplet has greater adherence to said tip well than to said portion of said wafer contacting said droplet.

23. The scanner of claim 1, wherein the surface area of the portion of said concave tip well that contacts said droplet is larger than the surface area of the portion of said wafer that contacts said droplet.

24. The scanner of claim 1, said scanner being a horizontal scanner for scanning said lower surface of said wafer in a horizontal orientation, and said relative movement between said droplet and said wafer creates a spiral pattern therebetween.

25. The scanner of claim 11, said single droplet of testing reagent positioned within a tip well of a droplet cup tip of a droplet cup, wherein the surface area of the portion of said tip well contacting said droplet is larger than the surface area of the portion of said wafer contacting said droplet.

26. The scanner of claim 11, said relative movement between said single droplet and said wafer creating a spiral pattern therebetween.

27. The dual-configuration scanner of claim 17, said testing reagent positioned within a tip well of a cup tip of a cup, wherein the surface area of the portion of said tip well contacting said testing reagent is larger than the surface area of the portion of said wafer contacting said testing reagent.

* * * * *